(12) United States Patent
Summer

(10) Patent No.: US 9,808,371 B2
(45) Date of Patent: Nov. 7, 2017

(54) MULTILEVEL ORAL APPLIANCE AND METHOD FOR MAINTAINING A PHARYNGEAL AIRWAY

(71) Applicant: John D. Summer, Portland, OR (US)

(72) Inventor: John D. Summer, Portland, OR (US)

( * ) Notice: Subject to any disclaimer, the term of this patent is extended or adjusted under 35 U.S.C. 154(b) by 813 days.

(21) Appl. No.: 13/831,105

(22) Filed: Mar. 14, 2013

(65) Prior Publication Data

US 2013/0199542 A1     Aug. 8, 2013

Related U.S. Application Data

(63) Continuation-in-part of application No. 13/310,601, filed on Dec. 2, 2011.

(60) Provisional application No. 61/458,759, filed on Dec. 2, 2010, provisional application No. 61/459,252, filed on Dec. 10, 2010, provisional application No. 61/796,657, filed on Nov. 16, 2012.

(51) Int. Cl.
    *A61F 5/56*     (2006.01)
(52) U.S. Cl.
    CPC .................................. *A61F 5/566* (2013.01)
(58) Field of Classification Search
    CPC ... A61F 5/566; A61F 5/56; A61C 7/08; A61B 5/682; A61B 17/24; A61M 16/049
    USPC ........ 128/845, 848, 859, 860; 433/6, 18, 19, 433/21, 140; D24/180; 600/240; 602/902
    See application file for complete search history.

(56) References Cited

U.S. PATENT DOCUMENTS

| | | |
|---|---|---|
| 4,198,967 A | 4/1980 | Dror |
| 4,505,672 A | 3/1985 | Kurz |
| 4,676,240 A | 6/1987 | Gardy |
| 4,884,581 A | 12/1989 | Rescigno |
| 4,969,822 A | 11/1990 | Summer |
| 5,066,226 A | 11/1991 | Summer |
| 5,176,618 A | 1/1993 | Freedman |
| 5,373,859 A | 12/1994 | Forney |
| 5,465,734 A | 11/1995 | Alvarez et al. |

(Continued)

FOREIGN PATENT DOCUMENTS

WO     WO 2006/125216     11/2006

OTHER PUBLICATIONS

International Search Report dated Sep. 28, 2007, issued by the International Searching Authority in corresponding PCT Application No. PCT/US06/019759, filed May 18, 2006.

(Continued)

*Primary Examiner* — Tarla Patel
*Assistant Examiner* — Caitlin Carreiro
(74) *Attorney, Agent, or Firm* — Klarquist Sparkman, LLP

(57) ABSTRACT

Plural tongue gripping projections coupled to upper and lower supports grip and hold the tongue during sleep and minimize the risk of the tongue slipping back and blocking the throat. One or both of the upper and lower supports are biased together. A tongue depressor extends rearwardly and downwardly from a cross member portion of a jaw coupler. A soft palate engager extends rearwardly from the cross member. The tongue grasping device, tongue depressor and soft palate engager cooperatively resist closing of the user's pharyngeal airway. The tongue depressor and soft palate engager are desirably biased apart and supported by flexible supports to permit movement of the rear of the tongue to close the pharyngeal airway during swallowing.

24 Claims, 15 Drawing Sheets

(56) References Cited

U.S. PATENT DOCUMENTS

| | | | |
|---|---|---|---|
| 5,592,951 | A | 1/1997 | Gastagnaro et al. |
| 5,649,540 | A | 7/1997 | Alvarez et al. |
| 5,715,840 | A | 2/1998 | Hall |
| 5,915,385 | A | 6/1999 | Hakimi |
| 5,964,588 | A | 10/1999 | Cleary |
| 6,109,265 | A | 8/2000 | Frantz et al. |
| 6,241,521 | B1 | 6/2001 | Garrison |
| 6,837,246 | B1 | 1/2005 | DeLuke |
| 6,955,172 | B2 | 10/2005 | Nelson et al. |
| 7,451,767 | B2 * | 11/2008 | Keropian ................ A61F 5/566 128/848 |
| 2003/0190575 | A1 * | 10/2003 | Hilliard .................. A61C 7/00 433/6 |
| 2008/0188947 | A1 | 8/2008 | Sanders |
| 2009/0126742 | A1 * | 5/2009 | Summer ................ A61F 5/566 128/848 |
| 2011/0178439 | A1 | 7/2011 | Irwin et al. |
| 2011/0226264 | A1 | 9/2011 | Friedman et al. |
| 2012/0138071 | A1 | 6/2012 | Summer |

OTHER PUBLICATIONS

Written Opinion dated Sep. 28, 2007, issued by the International Searching Authority in corresponding PCT Application No. PCT/US06/019759, filed May 18, 2006.

Office action dated Apr. 29, 2010, issued in corresponding U.S. Appl. No. 11/986,044, filed Nov. 17, 2007.

Office action dated May 25, 2011, issued in corresponding U.S. Appl. No. 11/986,044, filed Nov. 17, 2007.

* cited by examiner

ND METHOD FOR MAINTAINING A PHARYNGEAL AIRWAY

MULTILEVEL ORAL APPLIANCE AND METHOD FOR MAINTAINING A PHARYNGEAL AIRWAY

CROSS REFERENCE TO RELATED APPLICATIONS

This application is a continuation-in-part of U.S. application Ser. No. 13/310,601, filed Dec. 2, 2011, and entitled TONGUE RETAINER, which claims the benefit of U.S. Provisional Application Ser. No. 61/458,759, filed Dec. 2, 2010, entitled "INTRA-ARCH SOURCE OF BIASING FOR TETHERED TONGUE GRIPPING SURFACES"; and the benefit of U.S. Provisional Application Ser. No. 61/459,252, filed Dec. 10, 2010, entitled "ADJUSTABLE TONGUE REAR DEPRESSOR". This application also claims the benefit of U.S. Provisional Application Ser. No. 61/796,657, filed Nov. 16, 2012, entitled OROPHARYNX AIRWAY PROTECTION DEVICE.

TECHNICAL FIELD

The technology disclosed herein relates to maintaining a pharyngeal airway open, while permitting swallowing by the individual.

BACKGROUND

The prior art describes a number of devices designed to prevent snoring and/or obstructive sleep apnea by holding the lower jawbone forward. Holding the lower jawbone forward creates some additional space in the pharynx. Generally, obstructive sleep apnea is caused not by lack of pharyngeal space, but by the tongue dropping back and blocking the pharyngeal airway and by the distal or back end of the soft palate being sucked into the space between the rear of the tongue and the back wall of the pharynx. Holding the lower jaw forward exerts some forward influence on the resting position of the tongue, since the tongue is attached to the lower jawbone. However, the tongue is only loosely attached to lower jawbone, so holding the lower jawbone forward does not necessarily hold the tongue far enough forward to prevent obstructive sleep apnea. Holding the jaw forward also does not prevent the back or distal end of the soft palate from blocking the pharyngeal airway.

There is a need for an improved apparatus for resisting closing of an individual's airway to reduce the risk of sleep apnea.

SUMMARY

In certain embodiments, an apparatus grasps the front portion of an individual's tongue by squeezing it from above and/or from above and below between tongue gripping surfaces. The device then restrains the tongue from retrusion. In addition, a tongue depressor is positioned to engage the upper surface of a rear portion of the user's tongue to assist in opening the airway. In certain embodiments, the position of the tongue engaging portion of the tongue depressor is adjustable. Also, a soft palate elevator is positioned to engage the lower surface of the user's soft palate to assist in maintaining the airway open. Thus, a multilevel approach is used to maintain the pharyngeal airway in an open state.

The tongue gripping surfaces can be comprised of plural projections, such as a large number of densely arranged points or blades; and more desirably, a multiplicity of closely spaced needle-like projections. The projections, or selected portions thereof, can be supported at a forwardly extending angle toward the tip of the tongue. A biasing force provided by one or more biasing members urges one or more of the tongue gripping surfaces toward one another to grip the tongue. Because of the effectiveness of the tongue gripping surfaces, the tongue retainer can hold the tongue securely all night without compressing the tongue in a manner that causes pain or discomfort. For example, although variable, tongue compression forces of one-half pound or even less, can be sufficient to restrain the tongue.

In another exemplary embodiment, the upper tongue gripping surface is carried by an upper support pivotally coupled to an upper jaw coupler. The jaw coupler can comprise a dental appliance, mouthpiece or upper denture. The lower tongue gripping surface is supported by a lower support that is coupled to a lower jaw coupler. The lower support can be fixed or pivotally coupled to the lower jaw coupler. The upper support can be biased downwardly relative to the upper jaw coupler toward the lower support.

The upper support in one desirable embodiment is pivoted to the upper jaw coupler such as by a tether extending from a central to rear portion of the upper support to a front portion of the upper jaw coupler. As a result, both the front and rear ends of the upper support and associated upper tongue gripping surface can move upwardly and downwardly to maintain a grip on the user's tongue if the user opens his or her mouth somewhat, such as during sleep. The tongue depressor and soft palate elevator or engager are also included in this embodiment. Desirably the tongue depressor and soft palate elevator are supported by a cross member portion of the upper jaw coupler, such as a hard palate engaging portion. Exemplary embodiments can restrain the tongue from retruding beyond its normal resting posture and can be worn comfortably during sleep. Again, these embodiments desirably grasp the tissue of the front portion of the tongue so effectively that little compressive force is needed to hold the tongue securely for an extended time period, such as all night. Exemplary embodiments are desirably easily openable for insertion or removal of the tongue. Less desirably, the tongue gripping surfaces can be eliminated from an appliance while the appliance includes the tongue depressor and soft palate engagement features.

In a multi-level approach, a tongue is grasped and held, depressed at a rear portion thereof, and a portion of the soft palate is engaged and elevated or supported to resist closing of the pharyngeal airway of a user.

In accordance with an embodiment, a tongue grasping and restraining device holds the front portion of the tongue securely during sleep in order to minimize the risk of the tongue slipping back and blocking the throat. The tongue front portion is held by plural tongue gripping projections coupled to upper and lower supports. One or more of the upper and lower supports are biased together into a tongue engaging position. A tongue depressor extends rearwardly (toward the back of a user's mouth) and downwardly (toward the user's throat) from a cross member or upper palate engaging portion of a jaw coupler. A soft palate engager extends rearwardly from the cross member or upper palate engaging portion. The tongue depressor engages a rear portion of the user's tongue and the palate engager engages the user's soft palate. The tongue depressor and soft palate engager cooperatively urge the user's airway open. The tongue depressor and soft palate engager are desirably biased apart. As another aspect of an embodiment, the tongue depressor and soft palate engager are desirably supported by flexible supports to permit movement of the rear of the tongue and closing of the pharyngeal airway during swallowing action by the user. The front to rear position of the tongue depressor can be adjustable. In addition, the front to rear position of the soft palate engager can also be adjustable. The soft palate engager can comprise one or more enlarged soft palate engaging structures. In one exemplary embodiment, the soft palate engager comprises a soft palate engaging structure comprising a soft palate engaging surface of a rounded form positioned along the midline of the user's mouth. The tongue depressor can also comprise one or more enlarged tongue engaging structures. One exemplary embodiment of tongue depressor comprises at least one pair of spaced apart tongue engaging structures that each comprise a rounded tongue engaging surface, with one such tongue engaging surface being positioned at each side of the midline of the user's mouth to assist in maintaining the airway. The soft palate engaging surface can comprise a softer material than the tongue engaging surfaces. The soft palate engager can be biased against the soft palate with a lesser force than the biasing force of the tongue depressor against the tongue. The upper support is desirably coupled to the user's upper jaw, for example, to a denture, dental appliance or other form of an upper jaw coupler and can be pivoted thereto. The upper palate engaging portion or cross member can comprise a portion of the upper jaw coupler. The lower support can be hinged to, fixed to, or otherwise joined to a lower jaw coupler. A tube and rod mechanism in one embodiment couples the upper and lower jaw couplers together and can be used to cause the lower jaw to protrude relative to the upper jaw.

Various embodiments can be comprised of combinations and subcombinations of the above and following features and aspects.

In accordance with an embodiment, an apparatus is disclosed for grasping and restraining a front portion of the tongue of a user, engaging a rear portion of the tongue of the user, and engaging the soft palate of a user rearwardly of the hard palate of the user so as to resist closing of the pharyngeal airway of the user. The apparatus comprises a first upper support that comprises an upper support body portion comprising an upper surface, a lower surface, a front, a rear, and first and second sides, the first upper support also comprising a first tongue gripping surface. The first tongue gripping surface comprises a plurality of tongue engaging projections that extend from the lower surface of the upper support body portion toward the upper surface of a front portion of the tongue of a user. An upper jaw coupler is adapted to couple the first support to the upper jaw of the user, wherein the upper support body portion is pivotally coupled to the upper jaw coupler such that the front and rear of the upper support body portion is movable upwardly and downwardly relative to the upper jaw coupler. The upper jaw coupler also comprises an upper cross member portion for positioning adjacent to at least a portion of the hard palate of the user. The apparatus of this embodiment further comprises a second lower support that comprises a lower support body portion comprising an upper surface, a lower surface, a front, a rear, and first and second sides. The second lower support also comprises a second tongue gripping surface. The second tongue gripping surface comprises a plurality of tongue engaging projections that extend from the upper surface of the lower support body portion toward the lower surface of the front portion of the tongue of a user. A lower jaw coupler is adapted to couple the second support to the lower jaw of the user. At least one biasing member is coupled to at least one of the first and second supports and adapted to urge at least one of the first and second tongue gripping surfaces toward the other of the first and second tongue gripping surfaces with a front portion of a user's tongue positioned therebetween so as to grasp and restrain the tongue of the user. A tongue depressor projects from the upper palate engaging portion of the upper jaw coupler to a position for engaging and depressing the rear portion of the user's tongue. Also, a soft palate engager projects from the upper palate engaging portion of the upper jaw coupler to a position for engaging a portion of the soft palate. In this embodiment, the tongue depressor and soft palate engager are adapted to urge the rear surface of the tongue and the engaged portion of the soft palate away from one another so as to resist closing of the pharyngeal airway of the user.

As an aspect of an embodiment, the second lower support can be fixed to the lower jaw coupler. As an alternative, the second lower support body portion can be pivotally coupled to the lower jaw coupler such that the lower support body portion is movable upwardly and downwardly relative to the lower jaw coupler.

As a further aspect of an embodiment, a tether can pivotally connect the upper support body portion to the front of the upper jaw coupler. In addition, the tether can be connected to the first upper support at a location intermediate to the front and rear of the upper support body portion. In one form, the tether can be connected to the upper surface of the upper support body portion at a location that is at or rearwardly of the center of the upper support body portion.

As yet another aspect of an embodiment, an apparatus can comprise first and second telescoping mechanisms positioned along respective sides of the upper and lower jaw couplers, such as tube and rod mechanisms operable to adjust the protrusion of the lower jaw of a user of the apparatus.

As another aspect of an embodiment, the at least one biasing member can be coupled to the upper jaw coupler and to the upper surface of the upper support body portion so as to urge the first upper support downwardly toward the second lower support at least when the user's mouth is closed.

As a further aspect, the tongue depressor can be movable relative to the upper palate cross member portion at least in upward and downward directions. The tongue depressor in an embodiment can also be movable, such as slidable, relative to the upper cross member portion in front to rear directions.

As another aspect of an embodiment, the tongue depressor can comprise at least one elongated tongue depressor support arm with a first tongue depressor support arm portion mounted to the upper cross member portion and a second distal tongue depressor support arm end portion spaced from the upper cross member portion, and at least one enlarged tongue engager mounted to the second distal tongue depressor support arm end portion. The tongue depressor support arm can comprise a bendable material, wherein bending the tongue depressor support arm downwardly relative to the upper cross member portion shifts the tongue engager downwardly and bending the tongue depressor support arm upwardly relative to the upper cross member portion shifts the tongue engager upwardly.

As a further aspect of an embodiment, the soft palate engager can be movable relative to the upper cross member portion at least in upward and downward directions toward and away from the soft palate of the user. The soft palate engager in an embodiment can also be movable relative to the upper cross member portion in front to rear directions, rear to front directions, and upward and downward directions. In one form, the soft palate engager is slidably coupled to the upper cross member body portion. As another aspect, the soft palate engager can comprise at least one elongated soft palate engager support arm with a first soft palate arm portion mounted to the upper cross member portion and a second distal soft palate arm end portion spaced from the upper cross member portion, and at least one enlarged soft palate engager mounted to the second distal soft palate arm end portion. The soft palate engager support arm can comprise a bendable material, wherein bending the soft palate engager support arm downwardly relative to the upper palate engaging portion shifts the soft palate engager downwardly and bending the soft palate support arm upwardly relative to the upper cross member portion shifts the soft palate engager upwardly.

According to one aspect of an embodiment, the tongue depressor can comprise at least one of resilient band supports, a spring, and magnets operable to bias the tongue depressor away from the soft palate engager.

As a further aspect of an embodiment, a bendable tongue depressor mount can mount the tongue depressor to the upper cross member portion and a bendable soft palate engager mount can mount the soft palate engager to the upper cross member portion. The tongue depressor mount and soft palate engager mount can be operable to permit movement of the rear of the tongue and the soft palate to allow closing of the pharyngeal airway during swallowing by the user.

As a still further aspect of an embodiment, the tongue depressor can comprise at least one enlarged tongue engager with a tongue engaging surface for engaging the rear portion of the tongue of the user, wherein the soft palate engager comprises at least one enlarged soft palate engager with a soft palate engaging surface for engaging the soft palate of the user, the soft palate engaging surface being softer than the tongue engaging surface.

A yet another aspect of an embodiment, the tongue depressor can comprise a first tongue engager with a first tongue engaging surface and a second tongue engager with a second tongue engaging surface, the first and second tongue engaging surfaces being positioned to engage the tongue of the user on opposite sides of the center or midline of the tongue, and wherein the soft palate engager comprises one enlarged soft palate engager with a soft palate engaging surface positioned to engaging the soft palate of the user at a location along the center of the soft palate.

As a further aspect of an embodiment, the tongue depressor and soft palate engager respectively apply pressure to the respective rear tongue tissue surface and soft palate tissue surface with a lower pressure being applied to the soft palate tissue surface than to the rear tongue tissue surface. These components can be resiliently supported and biased away from each other. In an example, these components are spring biased against the respective contacted tissues.

In accordance with an embodiment, an apparatus is disclosed for grasping and restraining a front portion of the tongue of a user, engaging a rear portion of the tongue of the user, and engaging the soft palate of a user rearwardly of the hard palate of the user so as to resist closing of the pharyngeal airway of the user. The apparatus of this embodiment comprises a first upper support; the first upper support comprising a first tongue gripping surface, the first tongue gripping surface comprising a plurality of tongue engaging projections that extend toward the upper surface of the tongue of a user; an upper jaw coupler adapted to couple the first support to the upper jaw of the user, the upper jaw coupler comprising an upper hard palate engaging portion; a second lower support; the second lower support comprising a second tongue gripping surface, the second tongue gripping surface comprising a plurality of tongue engaging projections that extend toward the lower surface of the tongue of a user; a lower jaw coupler adapted to couple the second support to the lower jaw of the user; at least one biasing member coupled to at least one of the first and second supports and adapted to urge at least one of the first and second tongue gripping surfaces toward the other of the first and second tongue gripping surfaces with the user's tongue positioned therebetween so as to grasp and restrain the tongue of the user; a tongue depressor mounted at a first location to upper hard palate engaging portion and projecting rearwardly and downwardly relative to the first location; a soft palate engager mounted at a second location to the upper hard palate engaging portion and projecting rearwardly relative to the second location; and wherein the tongue depressor and soft palate engager are adapted to urge the rear surface of the tongue and the engaged portion of the soft palate away from one another so as to resist closing of the pharyngeal airway of the user. The first location can be below the second location.

Also, the tongue depressor can be movable, such as slidable, relative to the upper hard palate engaging portion in a front to rear direction, in a rear to front direction, and in upward and downward directions; and the soft palate engager can be movable relative to the upper hard palate engaging portion in at least upward and downward directions.

The tongue depressor can comprise at least one elongated bendable tongue depressor support arm of a material that remains in a bent position following bending. The tongue depressor support arm can comprise a first tongue depressor support arm end portion fixed to or slidably coupled to the upper hard palate engaging portion at the first location and a second distal tongue depressor support arm end portion spaced from the first location. At least one enlarged tongue engager can be mounted to the second distal arm end portion. The soft palate engager can comprise at least one elongated bendable soft palate engager support arm of a material that remains in a bent position following bending. The soft palate engager support arm can comprise a first soft palate engager support arm end portion mounted to the upper hard palate engaging portion at the second location and a second distal soft palate engager support arm end portion spaced from the second location. At least one enlarged soft palate engager can be mounted to the second distal soft palate engager arm end portion.

As an aspect of an embodiment, an upper jaw assembly is disclosed for an apparatus for grasping and restraining the tongue of a user and for urging the rear portion of a tongue of a user away from the soft palate of a user. The upper jaw assembly can comprise: a first upper support; the first upper support comprising an upper support body portion comprising an upper surface, a lower surface, a front, a rear, and first and second sides, the first upper support also comprising a first tongue gripping surface, the first tongue gripping surface comprising a plurality of tongue engaging projections that extend from the lower surface of the upper support body portion toward the upper surface of the front portion of the tongue of a user; an upper jaw coupler adapted to couple the first support to the upper jaw of the user, the upper jaw coupler comprising a cross portion spanning the users mouth from one side thereof to the other, wherein the upper support body portion is pivotally coupled to the upper jaw coupler such that the front and rear of the upper support body portion are movable upwardly and downwardly relative to the upper jaw coupler; a tongue depressor coupled to the cross portion and projecting rearwardly and downwardly from the cross portion for engaging a rear portion of the upper surface of a user's tongue; and a soft palate engager coupled to the cross portion and projecting at least rearwardly from the cross portion for engaging the user's soft palate. The tongue depressor can be movable, such as slidable, relative to the cross portion in front to rear directions and rear to front directions and upward and downward directions. Also, a tether can be included to pivotally connect the upper support body portion to the front of the upper jaw coupler, the tether being connected to the first upper support at a location intermediate to the front and rear of the upper support body portion or at or rearwardly of the center of the upper support body portion.

In accordance with another aspect, an embodiment of a method of resisting closure of the pharyngeal airway of an individual comprises: holding the tongue of the user in a protruded position; depressing a rear portion of the user's tongue; pushing the soft palate away from the rear portion of the user's tongue; and wherein these acts are simultaneously performed to urge the pharyngeal airway to an open state.

As a further aspect of a method embodiment, the method can comprise the act of resiliently depressing the rear portion of the user's tongue and resiliently pushing the soft palate away from the rear portion of the user's tongue with a force that is overcome by swallowing by the user such that the pharyngeal airway is closable during such swallowing.

In accordance with another embodiment, a multilevel oral appliance is disclosed for resisting closure of the pharyngeal airway of a user of the appliance, the appliance comprising: a tongue protrusion mechanism comprising a first tongue gripping portion coupled to the upper jaw of the appliance user and a second tongue gripping portion coupled to the lower jaw of the appliance user, the tongue protrusion mechanism comprising at least one biasing member operable to bias the first and second tongue gripping portions toward a tongue gripping position to hold the tongue of the appliance user in a protruded position; a rear tongue portion depressing mechanism coupled to the tongue protrusion mechanism and positioned to engage a rear surface portion of the tongue of the user of the appliance; and a soft palate elevating mechanism coupled to the tongue protrusion mechanism and positioned to engage and support the soft palate of the user of the appliance, the tongue depressing mechanism and soft palate elevating mechanism urging the engaged portion of the soft palate and engaged rear surface portion of the tongue away from one another.

As a further embodiment, an upper jaw coupler portion of a pharyngeal airway maintaining apparatus comprises: a support adapted for coupling to an upper jaw of a user of the apparatus; a tongue gripping element coupled to the support, the tongue gripping element comprising a tongue gripping surface with plural upper tongue surface engaging projections; and first and second tissue contacting members carried by the support, the first tissue contacting member being positioned to engage a rear surface of the tongue of the user at least during a portion of the time that the support is coupled to the upper jaw of the user, the first tissue contacting member being operable to apply a biasing force to the engaged rear surface of the tongue of the user, the second tissue contacting member being positioned to engage a portion of the soft palate of the user at least during a portion of the time that the support is coupled to the upper jaw of the user, the second tissue contacting member being operable to apply a biasing force to the engaged portion of the soft palate of the user. The first tissue contacting member can comprise a first elongated arm carried by the support and at least one tongue engager comprising a tongue engagement surface, the tongue engager being carried by the first elongated arm, the tongue engager being positioned such that the tongue engagement surface engages the rear surface of the tongue at least during a portion of the time that the support is coupled to the upper jaw of the user, the first elongated arm biasing the engaged tongue engagement surface against the engaged rear surface of the tongue. In addition, the second tissue contacting member can comprise a second elongated arm carried by the support and at least one soft palate engager comprising a soft palate engagement surface, the soft palate engager being carried by the second elongated arm, the soft palate engager being positioned such that the soft palate engagement surface engages a portion of the soft palate of the user at least during a portion of the time that the support is coupled to the upper jaw of the user, the second elongated arm biasing the engaged portion of the soft palate engagement surface against the engaged mid-portion of the soft palate. As another aspect, the soft palate engagement surface and tongue engagement surface can both be smooth.

As a further aspect, first and second elongated arms can respectively support a tongue engager and a soft palate engager. The arms can comprise spring arms that apply a biasing force that allows movement of the tongue engager and soft palate engager toward one another to close the pharyngeal airway during swallowing by the user.

As yet another aspect, the tongue engager can comprise at least one pair of first and second spaced apart tongue engagement elements positioned on opposite sides of the center or midline of the rear portion of the tongue of the user. The first and second spaced apart tongue engagement elements can be comprised of a polymer material and positioned sufficiently close to one another to resist the tongue of the user filling the space between the first and second spaced apart tongue engagement elements. Also, the soft palate engager can comprise a single soft palate engagement element for positioning approximately along the center of the soft palate of the user. Also, the soft palate engagement element can have a soft palate engagement surface that is softer than the tongue engagement surfaces of the first and second tongue engagement elements.

As an aspect of an embodiment, a spring can couple a soft palate engager to a tongue engager, the spring biasing the soft palate engager and tongue engager away from one another and respectively toward the respective engaged portion of a user's soft palate and engaged rear surface of the tongue.

As a further aspect of an embodiment, soft palate and rear tongue tissue contacting members can comprise magnets of the same polarity, the soft palate and rear tongue tissue contacting members being positioned such that magnetic forces of the magnets cause the soft palate and rear tongue tissue contacting members to repel one another toward the tissue to be contacted.

These and other features of embodiments disclosed herein will become more apparent from the description below and the accompanying drawings. The disclosure is directed to all novel and non-obvious features and method acts as disclosed herein both alone and in all combinations and sub-combinations thereof. There is no requirement that specific features be included any one embodiment. The embodiment disclosed herein are exemplary.

DETAILED DESCRIPTION OF EXEMPLARY EMBODIMENTS

A number of exemplary embodiments of tongue grasping, rear tongue depressing and soft palate elevating and restraining devices are described below. The examples can be custom devices, which are typically made in a dental laboratory to fit a user's upper teeth or edentulous ridge as well as the lower teeth. In users who lack upper teeth, an upper denture plate can, for example, be used as an upper jaw coupling mechanism.

In this disclosure, the terms "a", "an", and "at least one" means both the singular and the plural. Thus, if two of a particular element are present, there is also a, an, and at least one of these elements that is present. In addition, the term "coupled" means both direct connections between elements and indirect connections of elements through one or more other elements. Also, a component is "embedded" in another component if at least a portion of the component is inserted into the other component. Also, the term "plural" encompasses two or more and the term "multiple" means many (e.g. at least one hundred). The term multiplicity in this disclosure means at least one thousand. The term "and/or" in connection with a list of items means the items individually, all of the items collectively, and all possible subcombinations of the items.

Figure 1A:
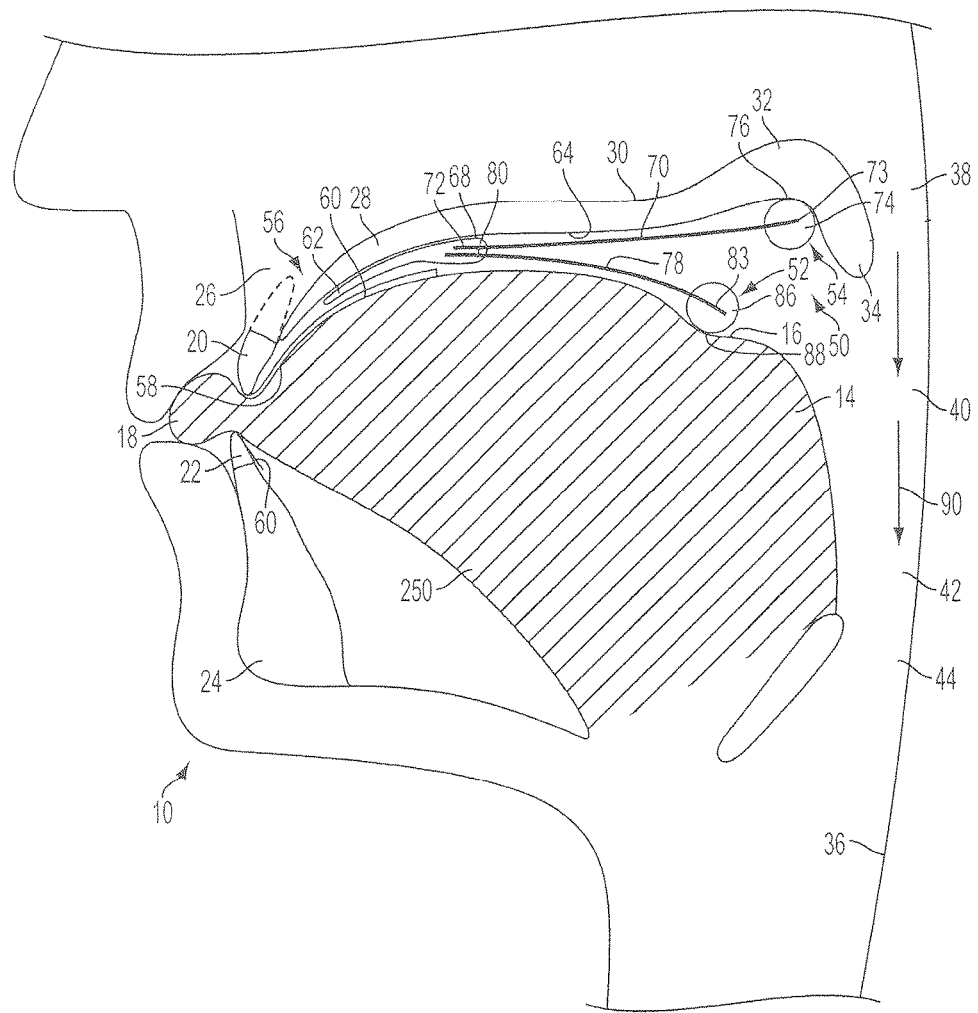
FIG. 1A shows a side view of a user's pharynx at rest while wearing a multi-level oral appliance in accordance with an embodiment of this disclosure, the multi-level appliance capturing the tongue in a protruded position, depressing a rear portion of the tongue, and elevating a portion of the soft palate.

FIG. 1A illustrates the basic anatomy of a typical head of an individual user of an appliance, indicated generally at 10. This anatomy includes a tongue 250 having a rear portion 14 with an upper rear surface 16. The tip or front end of the tongue 18 is shown protruding beyond the upper and lower front teeth 20, 22 of the user. In this example, the lower jaw 24 of the user is shown held in a position protruding slightly forward of the upper jaw 26 of the user (such as by tube and rod mechanisms, not shown). The user's tongue is indicated generally by the number 250 in FIG. 1A. The roof of the user's mouth is bounded in part by a hard palate 28 that extends rearwardly from the front of the user's mouth to a location indicated generally at 30, the location 30 being variable depending upon the anatomy of a particular user. A soft palate 32 extends rearwardly of the hard palate and terminates in a distal soft palate end portion 34. The pharyngeal wall or back wall of the pharynx of the user is indicated by the number 36. The location of the velopharynx of the user is indicated generally at 38, the location of the oropharynx of the user is indicated generally at 40, the location of the retroglossal pharynx of the user is indicated generally at 42, and the location of the hypopharynx or laryngopharynx of the user is indicated generally at 44.

Obstructive sleep apnea occurs when the tongue 250 drops back and contacts the back wall 36 of the pharynx directly and/or when the distal or back end 34 of the soft palate 32 gets sucked into the space between the rear of the tongue and the back wall of the pharynx. It can be difficult to determine which of these areas is the location of an obstruction in individual cases. Also, an obstruction frequently occurs in both areas during sleep. Therefore, it is highly desirable to be able to prevent both of these potential airway blockages using a single removable oral appliance that resists closing of the airway passage through the entire pharynx.

A device for holding the tongue and lower jawbone in a protrusive position and also depressing the rear of the tongue during sleep to prevent sleep apnea is desirable. Tongue and lower jawbone protrusion can be effective in maintaining an airway passage in the retroglossal (behind the tongue) pharynx 42 (including the oropharynx 40 and hypopharynx 44). However, the effectiveness of tongue and lower jawbone protrusion in maintaining an airway up one level higher in the retropalatal pharynx 38 (also known as the velopharynx) is variable. Tongue rear depression in combination with tongue and lower jawbone protrusion can be insufficient to maintain an airway passage through the retropalatal pharynx 38. That is, the very flexible tissue at the distal or back end 34 of the soft palate 32 can still get sucked in between a lower portion of the rear of the tongue 250, which has been pulled upward by tongue protrusion, and the back wall 36 of the pharynx. Thus it is desirable to combine tongue and lower jawbone protrusion and tongue rear depression with a mechanism for raising the distal end of the soft palate upward and moving the distal end forward. Upward movement of a portion of the soft palate at a location spaced from the distal end of the hard palate between the hard palate and end of the soft palate in effect tents or folds the soft palate as shown in FIG. 1A, to thereby both raise and pull the distal end of the palate forwardly. The terms upward and raise refer to a direction generally away from the tongue when the appliance is in a user who is standing. The term upper refers to the relative elevation or position of an element when the appliance is worn by a user who is standing. The terms lowered and downward refer generally to a direction away from a user's soft palate and toward the user's tongue when the appliance is worn by a user. The term lower refers to the relative elevation or position of an element when the appliance is worn by a user who is standing.

In addition, in a tongue grasping and restraining device that is attached to a denture to treat obstructive sleep apnea in people who have no teeth, a tongue depressing extension would produce a force that tends to destabilize the denture. That is, a tongue rear depressor creates a reciprocal bias upward on the back of the denture that tends to unseat the denture by flipping it down in front. The use of a soft palate elevator produces an opposed or reciprocal force downward on the back of the denture to compensate for the upward force on the back of the denture from a tongue depressor. This assists in stabilizing the denture in place.

A removable oral appliance employing tongue gripping and protrusion protects and assists in maintaining the airway through the oropharynx 40 and hypopharynx 42. Protection of the airway through the velopharynx 38 is provided by simultaneously depressing the rear portion 14 of the tongue and elevating a portion of the soft palate spaced inwardly from the distal end 34.

With reference to FIG. 1A, a soft palate and rear tongue spreading mechanism 50 can comprise a rear tongue surface engager 52 and a soft palate engager 54. The two engaging mechanisms 52, 54 are shown coupled to a tongue gripping mechanism 56. The illustrated tongue gripping mechanism comprises upper and lower jaw couplers (not shown) that support respective upper and lower tongue engaging surfaces 58, 60, such as explained below. The tongue gripping surface 58 is carried by a support 60 coupled to a portion 62 of the upper jaw coupler. The portion 62 can comprise a cross member extending transversely between the users teeth, such as from one side to the other of the user's mouth. The portion 62 can also comprise palate engaging portion of an upper jaw coupler of the appliance. By palate engaging portion it is meant that the upper surface of portion 62 can be positioned adjacent to or abutting the lower surface 64 of the hard palate 28 of the user 10. Spacing between the hard palate and portions of palate engaging portions can also be present. The upper soft palate engager 54 and rear tongue depressor 52 are shown mounted to a rear end portion 68 of the cross member 62. Exemplary embodiments are described in greater detail below. However, for purposes of illustration, the exemplary soft palate engager 54 is shown to comprise an elongated arm 70 having a forward or proximal end portion 72 mounted to the cross member 62 of the appliance. The arm 70 extends rearwardly, and in this case also upwardly, in the user's mouth toward the back of the user's throat. The soft palate support arm 70 also comprises a distal end portion 73 to which a soft palate engaging member or engager 74 is mounted. The soft palate engager 74 has a soft palate engagement surface 76 facing the engaged portion of the soft palate. In addition, in this embodiment, the rear tongue depressor 52 comprises an elongated arm 78 having a first or proximal end portion 80 mounted to the cross member 62 and a distal end portion 83 spaced rearwardly and downwardly from the end portion 68 of the cross member 62 to which the tongue depressor support arm 78 is mounted. A rear tongue surface engager 86 is shown coupled to the distal end 83 of the tongue depressor support arm 78. The illustrated tongue engager 86 comprises a tongue engagement surface 88 shown positioned to bear against the upper surface 16 of a rear portion 14 of the tongue 250.

The soft palate engager 74 and tongue engager 86 can comprise one or more engagement members. For example, tongue engager 86 can comprise one or more pairs of relatively firm and smooth tissue contacting shapes located on opposite sides of the center or midline of the user's mouth and tongue from one another. The side to side spacing of such elements in an embodiment can desirably be established so that the space between the elements cannot be filled in by the relatively firm tissue of the engaged surface portion of the rear of the tongue. This helps ensure the maintenance of an airway passage along the midline of the tongue between the tongue depressing elements. The soft palate engager 74 can comprise one or more elements, such as a single soft palate engagement element along the center midline of the soft palate. The combination of one or more pairs of tongue depressing elements and a midline upwardly directed soft palate engaging element also assists in maintaining an airway passage along the midline of the tongue during sleep by the user.

Figure 1B:
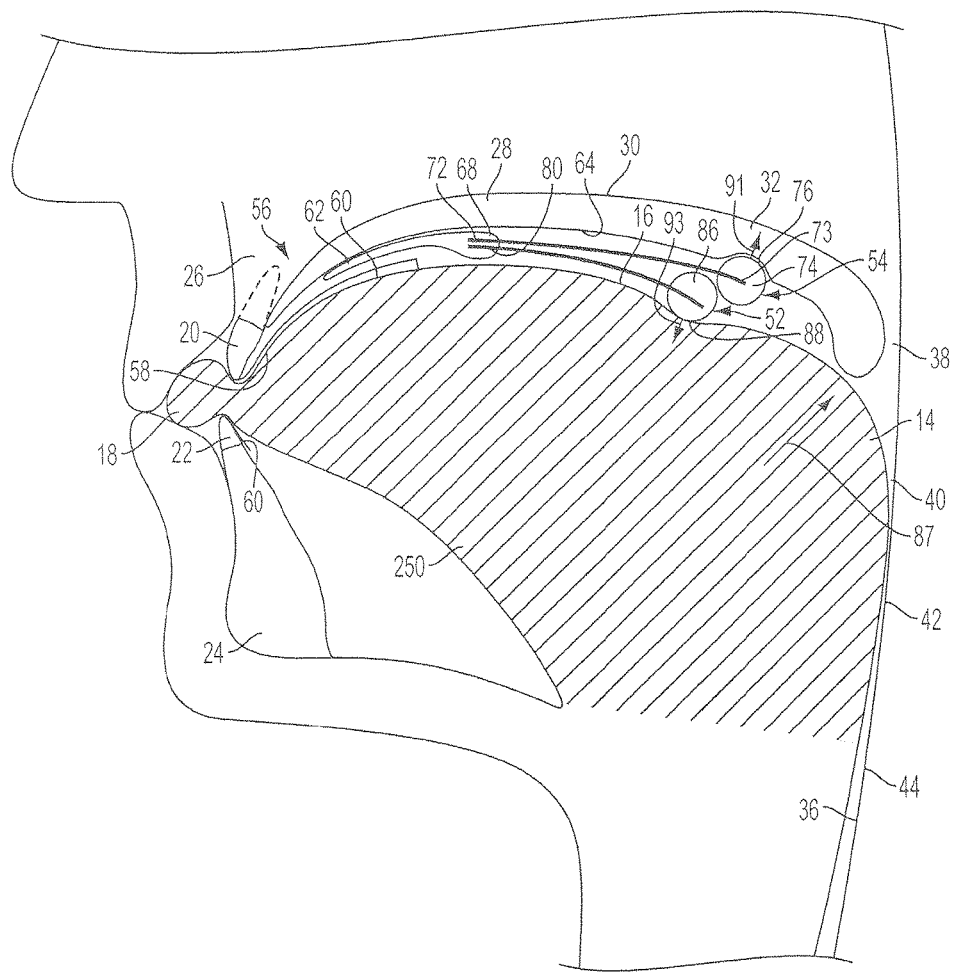
FIG. 1B shows a side view of the pharynx of the user during swallowing, while wearing an appliance in accordance with the embodiment of FIG. 1A, to illustrate that the appliance embodiment of FIGS. 1A and 1B allows the tongue to move and occlude the pharyngeal airway during swallowing.

Desirably, the soft palate engager 74 and tongue engager 86 are resiliently supported, such as by arms 70, 78 that can comprise flat springs. By utilizing flexible elements to support the respective tissue engagers 74 and 86, these support elements can move during swallowing by a user. For example, with reference to FIG. 1B, during swallowing, the tongue moves upwardly as indicated by arrow 87 and toward the back wall 36 of the pharynx with the tongue closing the pharynx during swallowing. By comparing FIG. 1A and FIG. 1B, it is apparent that in FIG. 1B the tissue engaging elements have moved closer together during this swallowing action. With reference to FIG. 1B, during a swallowing action, the muscular force of the rear portion of the tongue (upward and backward during swallowing) pushes the tongue rear tissue contacting element 86 as far upwardly as allowed by supporting arms 78. As a result of the backward movement of the rear of the tongue, the pharyngeal airway is temporarily occluded, but no air passage occurs during swallowing anyway. Allowing the arms 70, 78 to approach or abut one another during swallowing, when there is no inspiration of air occurring, allows the surrounding soft tissues to more easily accommodate the swallowing act without causing trauma to contacted soft tissues. In FIG. 1B, arrows 91 and 93 indicate the respective increased forces applied by the soft palate engager 74 against the soft palate and by the tongue engager 86 against the tongue rear surface as a result of movement of these elements during swallowing. When the tongue is at rest during sleep by the user and when swallowing is not occurring, the tissue engaging elements assume their positions shown in FIG. 1A to bias the tongue and soft palate to positions that assist in maintaining the airway, the airway being indicated by the number 90 in FIG. 1A.

Figure 2:
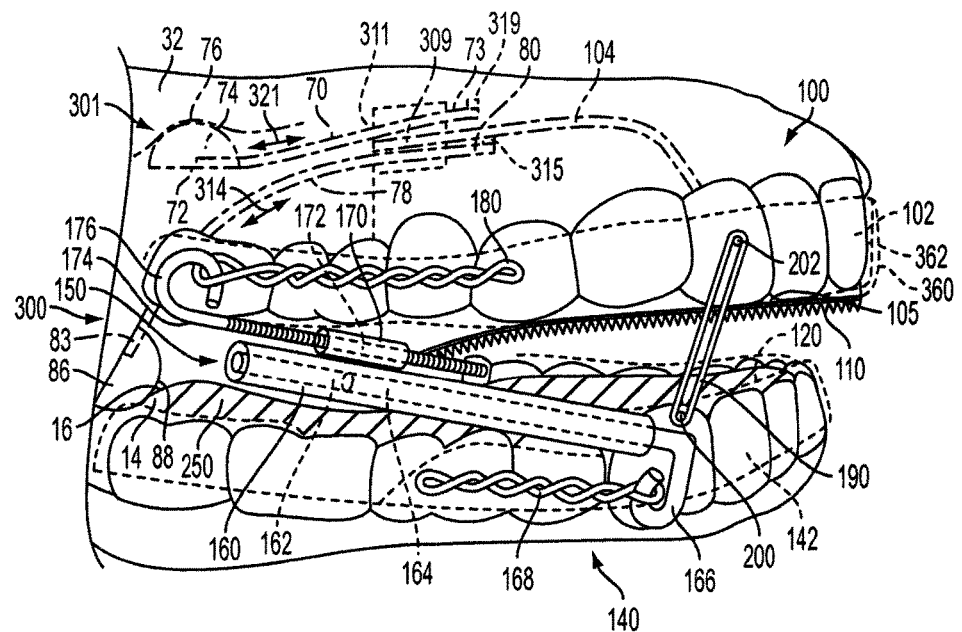
FIG. 2 is a side elevational view of one embodiment of a multi-level pharyngeal airway maintaining appliance comprising a tongue retaining mechanism, a rear tongue depressing mechanism, and a soft palate elevating mechanism.
Figure 3:
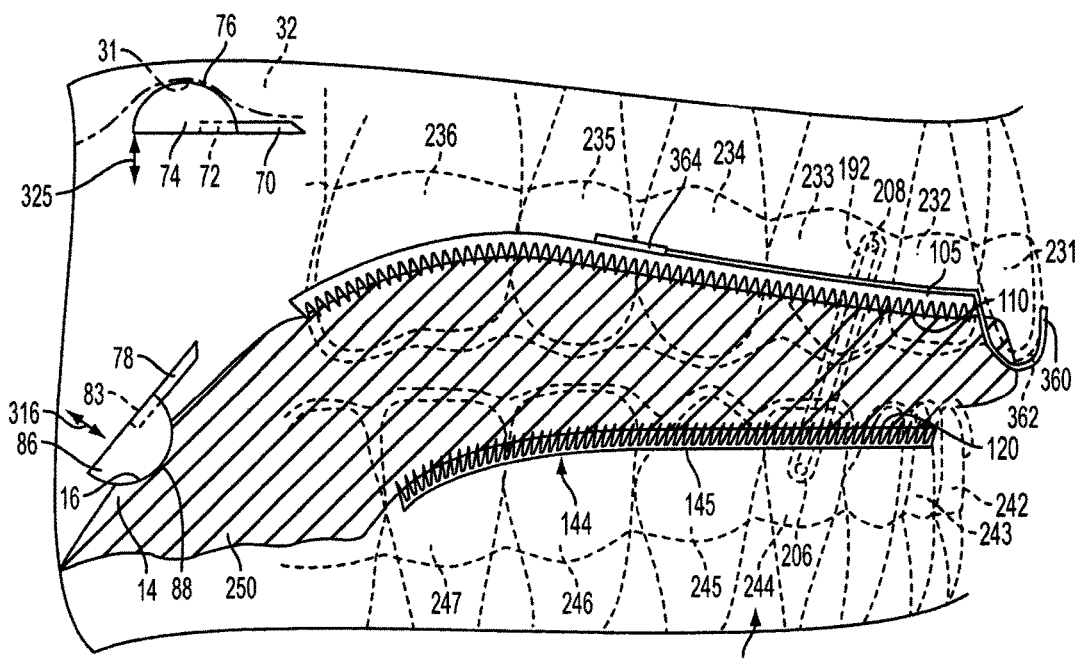
FIG. 3 is a vertical sectional side-view through a portion of the embodiment of FIG. 2, positioned in a user's mouth.
Figure 4:
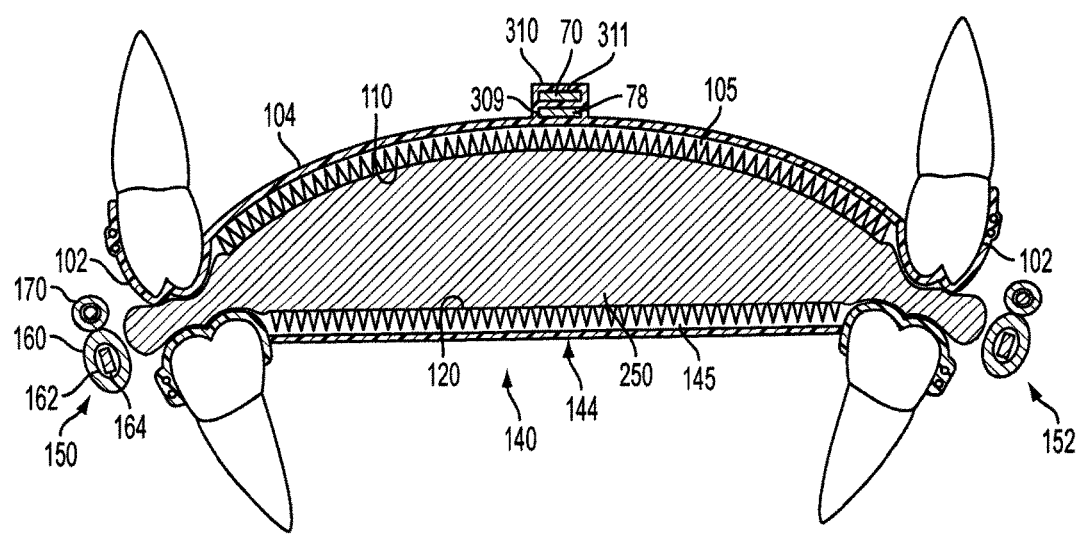
FIG. 4 is a transverse cross-sectional frontal view of the embodiment of FIG. 2, positioned in a user's mouth.

An exemplary tongue protrusion and tongue rear and soft palate separator embodiment, such as shown in FIGS. 2-4, is one embodiment that typically would be made by a dentist for a person with a full or nearly full dentition.

With reference to FIGS. 2-4, one form of an upper jaw coupler 100 is shown in the form of a dental appliance or mouthpiece having teeth receiving portions 102 for receiving the upper teeth of the user. The term "jaw coupler" (upper and lower) comprises a dental appliance or device that fits on or over, and/or otherwise engages, a user's teeth or the user's edentulous ridge after the teeth are removed. These devices can comprise, for example, a mouth piece, denture, and material anchored to a user's teeth. A crosspiece, plate or palate engaging portion 104 is joined to the teeth receiving portion. An exemplary upper support 105 for tongue gripping elements 110 for gripping the upper surface of the user's tongue is also shown. The upper support can be fixed relative to the upper jaw coupler. However, in a desirable form, the upper support 105 is movable relative to the jaw coupler, such as pivotally coupled to the jaw coupler as explained below. In this example, the appliance is designed to cover all or a portion of a user's upper teeth, including at least some teeth along both of the respective sides of the user's mouth. By covering all of the teeth, forces on the teeth resulting from protruding the jaw are evenly distributed. Appliances that cover the teeth of both upper and lower dental arches prevent adverse movement of all the teeth while also being able to hold the lower jaw bone forward relative to the upper jaw by means such as telescoping tube and rod mechanisms and/or by interlocking inclines.

One form of a tongue rear depressor 300 and soft palate engager 301 is also shown in FIG. 2. The illustrated tongue rear depressor is operable to engage the upper or dorsal surface of a user's tongue to push and hold the tongue away from the user's airway. The illustrated soft palate engager is operable to engage an under surface of the soft palate of a user, desirably at a location spaced inwardly from the distal end of the soft palate. The soft palate engager pulls the distal end of the soft palate upwardly and away from the back wall of the pharynx. As in the case of the embodiment of FIGS. 1A and 1B, in the embodiment of FIGS. 2-4, because the tongue depressor and soft palate engager desirably resiliently engage the respective upper surface of the tongue and lower surface of the soft palate so that they can move with the tongue during swallowing when airway protection (to prevent blockage thereof) is not needed.

In the embodiment of FIG. 2, the upper tongue gripping element support 105 for the tongue gripping surface 110 is coupled to the upper jaw coupler 102 so as to permit movement of the upper support 105 relative to the upper jaw coupler. More specifically, in this example, the support 105 can move upwardly and downwardly with the motion of the tongue to maintain contact with the tongue until such time as the mouth is opened wide enough to permit removal of the tongue retainer. More desirably, the upper tongue gripping element support is pivotally coupled to the upper jaw coupler, such as to a front portion of the upper jaw coupler. As one specific example of a pivotal connection, a tether 360 is shown (FIGS. 2 and 3) extending from the front portion of the upper jaw coupler beneath the front tooth 31 and covering portion 362 of the upper jaw coupler and across the upper surface of the upper tongue gripping element support 105 to a location 364 (FIG. 3) at which the tether is secured to the upper surface of upper support 105. The tether can comprise any suitable material, such as one or more strips of flexible mesh of a polymer material. Tether connection location 364 is desirably intermediate to or between the front and rear ends of the upper support 105 and is more desirably at a location that ranges from a central portion between the front and rear ends of the upper support 105, to a rear portion of the upper support. With this construction, if the lower jaw of the user drops, for example during sleep, both the front and rear portions of the upper support 105 (as well as the central portion thereof) can also drop to maintain contact between the gripping elements of tongue gripping surface 110 and the upper surface of the tongue. In addition, if the mouth is opened widely, the tongue will be free of both the upper and lower tongue gripping elements 110, 120 to permit removal of the tongue retainer.

Also, in this example (FIGS. 2-4) a lower jaw coupler 140 is also shown. The coupler 140 is shown in the form of a dental appliance or mouthpiece having teeth receiving portions 142 and a cross-piece, lingual plate or portion 144 (FIG. 3). In this example, the dental appliance 140 is designed to cover a portion or all of the user's lower teeth, including at least some teeth along both of the respective sides of a lower jaw. In operation, the lower dental appliance 140 can be held, along with the entire lower jaw bone of a user when teeth are received therein, in a protruded position, such as by respective telescopic mechanisms positioned along the respective sides of the apparatus. One specific example of such telescopic mechanisms comprises first and second tube and rod mechanisms (one being indicated at 150 in FIG. 2) along the sides of the teeth receiving portions of the jaw coupling appliances.

Figure 9:
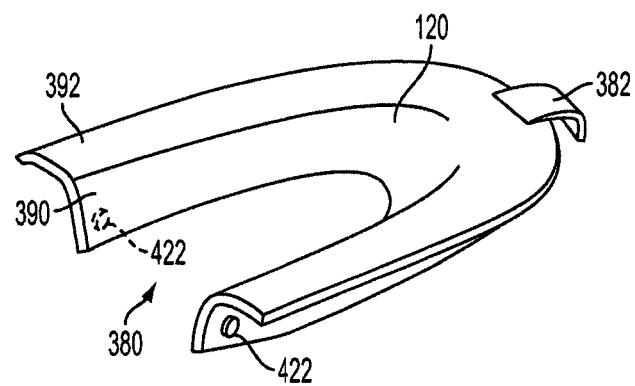
FIG. 9 is a perspective view of one form of a lower tongue gripping surface support.

Also, in the embodiment of FIGS. 2 and 3, the lower tongue gripping surface support 145 and the supported tongue gripping surface 120, can be fixed to the lower jaw coupler or, alternatively, can be movably coupled to the lower jaw coupler. For example, the lower support 145 can be pivoted to the lower jaw coupler, such as by a tether 382 (FIG. 9 shows an example thereof) embedded or otherwise secured to the lower jaw coupler and to the lower support 145. For example, the tether 382 can be secured to the lower jaw coupler at a location forwardly of the front of the lower jaw coupler, such as forwardly of the frontmost tooth 41. The tether can extend rearwardly across the biting surface of a lower tooth covering portion of the lower jaw coupler to a location that can be at or spaced rearwardly of the front edge of the lower support 145. Since the tongue moves with the lower jaw, the teeth gripping elements 120 of the lower support 145 naturally remain in contact with the tongue as a user opens his or her mouth slightly during sleep. For this reason, a tether, if used, can be connected more forwardly to the undersurface of the lower support 145 than the location 364 (FIG. 2) of the connection between tether 360 and the upper surface of upper support 105. As can be seen in FIG. 9, the lower support 380 can be of a generally U shape construction with a downturned lingual flange portion 390 that is positioned along the sides and underneath the user's tongue and with an upper flange portion 392 that can support the tongue gripping elements of gripping surface 120.

A lingual portion 145 of the lower jaw coupler that can be supported by portion 144 can support a tongue gripping surface 120 and can also be affixed to the lower jaw coupler 140 or to portion 144.

In the FIGS. 2-4 embodiment, the lower jaw can, for example, be held in protrusion by two tube and rod telescopic mechanisms 150, 152 (FIGS. 2 and 4). With reference to FIG. 2, one of such tube and rod mechanisms 150 will be described as an example. The mechanism comprises a first sleeve 160 that is elongated and defines a longitudinally extending bore 162 therethrough. A rod 164 is slidably received within bore 162. An end portion 166 of the rod adjacent to lower appliance 140, and near the forward end of the appliance, can comprise a hook that engages a loop of an anchor 168 embedded within the lower teeth receiving portion 142 of the appliance. A second sleeve 170 is mounted or coupled to sleeve 160, such as by welding, and can be stacked above the first sleeve. Sleeve 170 has a longitudinally extending bore 172 that is desirably threaded. A tube coupler 174 has an externally threaded shank portion that is threadedly received by the sleeve 170. Tube coupler 174 can be shaped to form a hook 176 at one end thereof. Hook 176 can engage a loop portion of an anchor 180 embedded in the teeth receiving portion of the appliance. With sleeve 160 disconnected from rod 164, the tubing assembly, including sleeves 160, 170 can be rotated in a first direction relative to the tube coupler 174 to shift hook 176 away from sleeve 170 to telescopingly lengthen the tube and rod mechanism. In contrast, rotation of the tubing assembly, including sleeves 160, 170 relative to the tube coupler 174 in the opposite direction shifts hook 176 toward sleeve 170 and shortens the length of the tube and rod mechanism. Although this construction is advantageous, other telescoping mechanisms, such as other forms of tube and rod mechanisms can also be used.

With reference to FIG. 4, the illustrated rod 164 desirably can have at least one anti-rotation surface, and in FIG. 4 the rod is rectangular in cross-section and thus has four such surfaces. In addition, the bore 162 also can have at least one anti-rotation surface, for example surfaces formed by the generally oval cross-sectional shape of the interior of the bore 162. Consequently, the interior of the bore surfaces engage flat surfaces of the rod and restrict the rod 164 against rotation relative to the sleeve 160. Thus, anti-rotational cooperating surfaces are provided in this tube and rod instruction. The tube and rod mechanisms couple the upper jaw coupler portion 100 of the dental appliance to the lower jaw coupler portion 140 in a manner that allows extension/contraction of the portions 100, 140 relative to one another. In this example, the anchors 168, 180 can be embedded, for example, in acrylic on the outer (buccal) portions of the teeth receiving components of the appliances. When the upper and lower components of the tube and rod mechanisms are engaged in the user's mouth, the rod 164 is positioned within the sleeve 160 and is telescopically reciprocable within the sleeve. As the user's mouth closes, the rod slides into the sleeve until the forward most open end of the sleeve abuts the hook 166 and halts the inward movement of the rod within the sleeve. This thereby halts the retrusive movement of the lower jaw bone relative to the upper jaw.

One or more biasing mechanisms can be provided for biasing at least one of the upper and lower portions 100, 140 toward the other or for biasing at least one of the upper or lower tongue gripping surface supports toward the other. For example, elastic bands, such as rubber bands 190, 192 (FIGS. 2, 3), can engage and be stretched between biasing member coupling extensions. Thus, for example, lower lingual buttons 200, 206 can project outwardly at opposed locations from an outer surface of appliance portion 140 with such buttons 200, 206 being positioned toward the front of the user's mouth. Similarly, lingual buttons 202, 208 can project outwardly from appliance portion 100 in opposed directions with such buttons 202, 208 being located toward the front of user's mouth such as slightly forwardly of buttons 200, 206 in this example. Elastic bands 190, 192, extend between respective pairs of the lingual buttons (e.g., band 190 extends between buttons 200, 202 and band 192 extends between buttons 206, 208). Lingual buttons are commonly used in orthodontics for attaching rubber bands. Other mechanisms can alternatively be used to attach biasing members, such as rubber bands or other biasing members, to upper and lower dental appliance portions. Examples comprise lingual cleats, loops of wire, and structural or anchoring components that are part of a dental appliance. The attachment mechanisms can be located on the outer aspects of the appliances to allow the tongue to fit comfortably between the rubber bands or other biasing mechanisms when they are stretched taut. Plural rubber bands can be used as exemplary biasing mechanisms on each side of the appliances. Orthodontic elastic bands have been found particularly useful. As a specific example, four two ounce (light) force ⅛ inch long latex elastic bands from Dexta Corporation of Napa, Calif. have been found to apply sufficient biasing force to urge the tongue gripping surfaces 110, 120 together for holding the tongue securely without causing pain or ischemia. In other examples described below, one or both the upper and lower gripping surface supports can be biased toward the other support without biasing mechanisms, such as bands, that interconnect the upper and lower jaw couplers.

In the lower jaw protrusion embodiment of FIGS. 2-4, the tongue gripping surfaces 110, 120 are separated for insertion or removal of the tongue simply by opening the user's mouth. This makes insertion and removal of the tongue easy.

The tongue gripping surfaces 110, 120 can be equipped with various mechanisms for frictionally engaging and grasping the user's tongue therebetween. The tongue gripping mechanisms desirably comprise a plurality of projections and most desirably include a multiplicity of such projections. The projections of tongue gripping surface 110 can be different from, identical to, or similar in part to, the projections of tongue gripping surface 120. Also, combinations of different types of projections can be used on either or both of the tongue gripping surfaces 110, 120.

Figure 6:
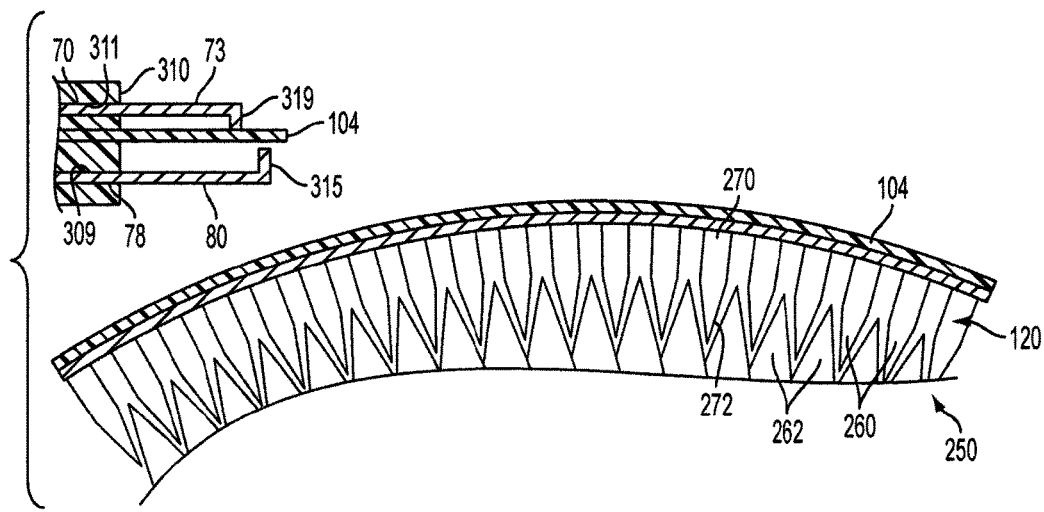
FIG. 6 shows an example of filiform papillae of a user's tongue in the process of engagement by projections of one form of an upper tongue gripping surface and also shows a portion of a cross member, which can comprise a palate engaging portion of an upper jaw coupler, to which a tongue depressor support arm and a soft palate engager support arm is mounted.

With reference again to FIGS. 2-4, the downward or tongue facing portion of upper tongue gripping surface 110 is desirably comprised of a large number of projections. These projections can be needle-like and can be configured to fit between the filiform papillae which occupy most of the upper (dorsal) surface of the front half of the tongue. These needles can be of any suitable material, such as of plastic or metal, with acrylic and stainless steel being specific examples. FIG. 3 illustrates projections of tongue gripping surface 110 bearing against the upper surface of the user's tongue 250 and projections of the gripping surface 120 bearing against the under surface of the tongue. FIG. 6 illustrates exemplary needle-like projections, some being numbered as 260, shown being positioned between filiform papillae 262 of the user's tongue as the tongue gripping surface 120 engages the upper surface of the tongue.

Figure 7A:
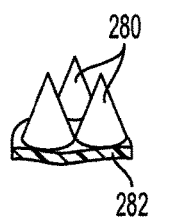
FIGS. 7A, 7B and 7C illustrate exemplary tongue gripping surfaces.
Figure 7B:
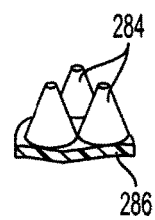
Figure 7C:
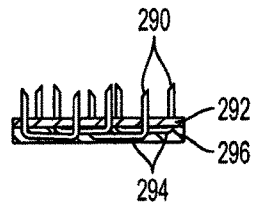

The projections can take many forms, in one specific example, like the filiform papillae, the needles can be about 0.1 inch long and about 0.03 inch in diameter at their bases. With such small diameters, a multiplicity of such gripping elements, such as two or three thousand or more of the needles, can fit on a surface the size of upper tongue gripping surface 120. Desirably, the density of such projections is at least about 500 per square inch. Although the ends of the individual needles can be very sharp, the large number of such needles provides a "bed of nails" effect that makes them safe to apply to the tissue of the upper surface of the tongue without the danger of cutting the tissue. In FIG. 6, exemplary projections each comprise a right cylindrical base portion 270 and a tapered conical needle-like tip portion 272. In the embodiment of FIG. 7A, the projections comprise conical projections 280 projecting from a base 282. In FIG. 7B, the projections comprise frustoconical projections 284 projecting from a base 286. In FIG. 7C, the projections comprise a plurality of staples, two of which are numbered as 290 in FIG. 7C. The staples of this example extend upwardly through a flexible base 292, such as a fabric with the crowns 294 (shown for two of such staples) being embedded in material, such as acrylic 296, coating and impregnating the fabric 292. Additional acrylic can be placed above the fabric as well. The construction of FIG. 7C can be affixed to, for example, the gripping surface support 105 of the upper portion of the appliance. Other examples of suitable projections are described below. Although the densely packed needle-like projections are desirable, the embodiments are not limited to the specific types or shapes of projections described herein.

As a specific example, about 4,000 needle-like bristles can be positioned on the upper tongue gripping surface and sized to fit between the filiform papillae that cover the top of the front of the tongue. In addition, a multiplicity of needle-like bristles that can be smaller in length and diameter than the upper bristles can be used to grip the lower surface of the tongue. More gripping elements can be placed on the lower gripping surface than the upper gripping surface in an embodiment. For example, about 11,000 of such lower bristles can be used in one example. The gripping elements are not limited to structures with needle-like projection structures as other surfaces can be used to grip the tongue.

FIG. 4 illustrates a cross-section, in a transverse plane through the upper and lower jaw protrusion components. As can be seen in FIG. 4, at least a portion of the tongue gripping surface 110 in this embodiment desirably is concave so that the tongue gripping surface more closely follows the curved curvature of the upper surface of the tongue 250. In the embodiment of FIG. 4, the lower tongue gripping surface 120 is shown as being straight in transverse cross-section. However, this surface can similarly be convex at least in part to more closely fit the contour of the undersurface of the user's tongue. With reference to FIG. 2, at least a portion of the upper tongue gripping surface 110 can also be concave in a front to back direction and in a side to side (transverse) direction to again closely follow the contour of the user's tongue. In addition, a portion of the lower gripping surface 120 can also be curved, for example convex, in a front to rear direction to more closely fit the lower surface of the user's tongue. It should be noted that these curvatures are not required but do assist in providing a greater surface area of the tongue gripping surfaces in contact with the tongue to thereby enhance the retention of the tongue between the tongue gripping surfaces. Desirably, the upper tongue gripping surface 110 shown in FIG. 4 extends laterally to fill the area of the tongue bounded by the upper teeth and rearwardly back to roughly the location of the first molar of the user's mouth. It is to be understood that the tongue gripping surface 110 can also extend laterally onto and over the biting surfaces of some of the teeth.

The projections of the upper and lower tongue gripping surfaces, or at least a plurality of such projections, can be angled forwardly to assist in tongue retention.

As alternatives, the tongue gripping surfaces can comprise numerous rows of blade-like projections, which can be skewed from one another, parallel to one another, and some of such blades desirably can extend in a transverse direction across the user's tongue. Desirably, although not required, the edges of the blades can be angled toward the tip of the tongue as they emerge from their supporting base so that the tongue cannot easily move backward from engagement in the space between the upper and lower tongue gripping surfaces. The upper projections and lower blades can, for example, project toward the tongue tip at a desirable angle. A specific example of a projection angle is an angle of from about 45 degrees to 85 degrees, with a 75 degree angle being a more specific example. The blades can have an edge which is desirably very thin, for example 0.1 inch or less with a specific example being 0.05 inch. The edges of the blades that contact the lower surface of the tongue can also be beveled to create a sharper edge that faces the tip of the tongue.

As a further exemplary manufacturing approach, multiple small areas of a substrate or panel can be partially cut out, leaving a hinge portion coupled to the panel, these cut areas can be pushed out, such as by using a stamping process so as to protrude as multiple projections from the surface of the panel. The projections can be angled toward the tip of the tongue. Yet another approach comprises cutting, or etching, transverse grooves in a substrate or panel to create a textured surface of projecting blades. As a further approach, strips of wire mesh can be cut to leave exposed mesh tips after embedding or fastening the strips to a base. The strips are yet another form of blade or tongue engagement projections. Small serrated blades such as jewelers saw blades mounted in a base have been found to be effective tongue gripping surface elements. Alternatively, plastic blades, such as of acrylic, can be fabricated by making a mold having a surface of saw blades, wetting the mold with acrylic monomer, and then filling the mold with polymer in the same manner as described above in connection with making needle-like projections on a tongue gripping surface. As yet another approach, strips of stainless steel mesh can be cut. The cut side edge of such strips will have projecting mesh wires. The opposite side edge can be embedded or secured to a base to comprise a tongue gripping surface of blades formed of such mesh strips.

As another specific example, numerous parallel densely arranged 0.01 inch thick stainless steel wires projecting downwardly from a base or from the denture can be used. As a specific example, at least several hundred lengths of wire protruding downwardly into the tissue at the top of the tongue from a base affixed to or supported by an upper jaw coupler 100 can be used. Wires of up to 0.05 inch in diameter can also be used, as well as other cross sectionally dimensioned wires, but larger numbers of smaller diameter wires are more desirable. Such small wires more effectively engage the upper surface of the tongue because they fit between the filiform papillae which occupy most of the tongue upper surface.

With reference to FIG. 7C, the gripping projection can be made by first penetrating a flexible support, such as of fabric, with miniature staples and then embedding the fabric or support with the connecting portions (the crowns) of each staple in the acrylic of a denture. The staples can be made of stainless steel wire that is roughly, for example, 0.01 inch in diameter. The legs of the staples can be about 0.12 to 0.2 inches long and the crowns of the staples can be about 0.12 inch long. These dimensions can be varied. Although a specific example of a staple supporting base is fabric, the base can be made of any suitable material such as a poured resin. The base can be fixed or mounted to the downwardly facing surface of the upper denture or jaw coupler 100 or to an upper support 105, such as in a dental laboratory by embedding the base and crowns of the staples in dental acrylic.

With reference to FIG. 3, some of the user's upper teeth are shown with numbers 231, 232, 233, 234, 235 and 236. In addition, some of the user's lower teeth are shown with numbers 242, 243, 244, 245, 246 and 247. With reference to FIGS. 1 and 2, it can be seen in this exemplary embodiment that there can be a change in the angle of the plane or direction of the lower tongue gripping surface 120 such as at the location corresponding to teeth 246 and 247. To enhance the grip, the lower tongue gripping surface 120 can follow the natural curve of the underside of the tongue posteriorly down toward the base of the tongue in the user's neck. In FIG. 4, the lower tongue gripping surface 120 is depicted as flat, however it is understood that tongue gripping surface 120 can also have a concavity to fit the natural contour of the underside of the tongue.

A notch can be provided along the rearmost edge of lower tongue gripping surface 120 with the notch being centrally positioned relative to the lower tongue gripping surface support. The notch can be triangular or of other shapes. The notch is provided to accommodate the lingual frenum, a fiberous attachment between the underside of the tongue and the lower jaw bone. Alternatively, the support for the tongue gripping surface 120 can be shortened in the rearward direction to terminate forwardly of the lingual frenum with a notch then not being provided. As yet another alternative, a flexible membrane or other flexible component can be provided at such location to accommodate the lingual frenum.

Various approaches can be used to fabricate the projections of tongue gripping surfaces 110, 120, such as described in U.S. Published application Ser. No. 11/986,044 to Summer, entitled Tongue Grasping and Restraining Apparatus and Method, filed Nov. 17, 2007, which is incorporated herein in its entirety. One exemplary approach for fabricating needle-like projections of the upper tongue gripping surface 110 of the embodiment of FIG. 1 is described as follows. A plurality of mold forming pins, some of which are supported to project upwardly from a mold pin supporting base. Flexible molding material is utilized in this approach to take an impression of the surface formed by the collection of pin points or tips of the supported pins. The pins can be supported parallel to one another and angled in one direction relative to the base (this results in the molding of tongue engaging projection pins angled forwardly toward the tip of the tongue when the mold is used). The base can be a rigid base, such as one made of plaster and wax which holds the pins so that they do not pull out of the base when the fully set molding material is pulled off the collection of pin points. However, the base can also be a flexible base, such as a tightly woven nylon fabric, holding a collection of pins which are tightly enclosed by a surrounding framework, such as by a thick rubber band, so that the pins can freely move up and down relative to each other and thereby the plane of the pin tips can be adjusted to fit any desired surface contour by simply placing the flexible base supporting such pins on a surface with the appropriate contour.

In one approach to manufacturing the mold, a flexible molding material, such as polyvinylsiloxane, is placed or expressed onto and about 1 mm to 3 mm into the surface of the pin points of the supported pins, allowed to set, and removed. A base material, such as fabric cloth, can be placed over the polyvinylsiloxane after it has been expressed onto the pin points to receive some of the molding materials and give the mold tensile strength to facilitate removal of the mold without tearing it.

The resulting mold can then be used to form a tongue gripping surface. For example, the mold can be used to form a tongue gripping surface of acrylic or other plastic. As a specific example, the mold can be thoroughly wetted with acrylic monomer or other plastic solvent or polymerizing agent. A brush can be used to release trapped air bubbles from the mold. A powdered polymer can then be added to the wetted mold until a sufficiently thick mix of polymerized plastic, such as acrylic, is built up within the mold. Thus, a tongue gripping surface resulting from the use of the mold comprises plural needle-like points supported on an acrylic base. Adding polymer to a mold surface that has already been thoroughly wetted with monomer allows the material, such as acrylic, to reach the full depth made by the impression of the pin points in the mold and thereby create tongue gripping points that are almost as sharp as the pins, which can be comprised of steel, used to make the mold. Vibration can also be used to enhance the distribution of the powdered polymer into the monomer in the ends of the pin point mold depressions. A vacuum can be used to assist in removing trapped air bubbles. The pins can be of other shapes at their tips to result in a tongue gripping surface having alternative shapes.

For individuals without upper teeth, a suitable mechanism for attaching the tongue restraining apparatus to the upper jaw can be by means of an upper denture or base plate that maintains a good fit against the palate and edentulous ridge. The lack of upper teeth provides a great deal of clearance space for accommodating biasing mechanisms, such as torsion springs or other hardware, in an upper denture or base plate. Also, a well fitting upper denture or base plate provides sufficient anchorage to the upper jaw to resist retrusion of the tongue when the apparatus is in use.

Desirably, the use of upper and lower tongue gripping surfaces provides a frictional engagement of the tongue.

With reference to FIGS. 2, 3, 4, and 6, an embodiment of a tongue rear depressing device and of a soft palate engaging device are shown. The tongue depressor in this example is coupled to the cross member or palate engaging portion 104 of the upper jaw coupler 100 and projects rearwardly and downwardly from the support 104 toward the upper surface 16 of a rear portion 14 of the tongue 250 to depress the rear portion of the tongue rearwardly of the grip of the upper tongue gripping surface 110. The tongue depressor can be movably mounted to the upper support so that it can move in front and rear directions toward and away from the mouth of the user. Desirably the tongue depressor is movable downwardly and upwardly, for example by bending, toward and away from the tongue rear surface. The tongue depressor can be threadedly coupled to support 104 or slidable relative to the support as specific examples. The soft palate engager mechanism or assembly in this example is also coupled to the cross member or to a palate engaging portion 104 of the upper jaw coupler 100. The soft palate engager mechanism comprises a tissue engagement element or soft palate engager 74 supported at a location rearwardly and desirably upwardly from the support 104 such that the soft palate engager projects rearwardly into a position where it engages and elevates (moves it generally upwardly away from the tongue) a portion of the soft palate inwardly from the distal end of the soft palate. The soft palate engager can be movably mounted to the upper support, such as slidably or threadedly coupled thereto so that it can move in front and rear directions toward and away from the mouth of the user as well as upwardly and downwardly, for example by bending. However, in one alternative embodiment, the soft palate engager is in a fixed position relative to the support 104 with respect to front and rear motion port arm relative to the support cross member 104.

While jaw protrusion and tongue protrusion desirably protect the hypopharynx and oropharynx, they are not very effective in protecting the velopharynx where the rear portion of the tongue can drop back and make contact with the soft palate. One approach for protecting the velopharynx against blockage is by depressing the rear portion of the tongue and elevating or supporting a portion of the soft palate so that the soft palate and tongue tissues are held away from one another and away from the back wall of the pharynx.

Desirably, for effective treatment of obstructive sleep apnea, the entire pharyngeal airway is kept open for airway passage by protection against obstruction by soft tissues. One critical area of the airway passage is the area between the rear of the tongue (generally the portion between the vallate papillae and the root of the tongue in the area of the hypopharynx) and the soft palate. Opening of the airway passage is assisted by depressing the rear portion of the tongue so that it is held down and away from the soft palate and elevating the soft palate and drawing the soft palate away from the rear pharyngeal wall. The illustrated exemplary tongue depressor 300 and soft palate engager 301 is provided for this purpose. That is, adding a rearward tongue depressor extension to the upper support, such as to the palate engager 104 of a tongue retaining apparatus, provides a dual functioning tongue retainer, namely one that retains the tongue forwardly out of the airway and also that assists in opening the airway by depressing the rear of the tongue. In addition, adding a rearward soft palate elevator to the appliance, such as supported by the palate engager 104 of a tongue retaining apparatus, provides a triple functioning tongue retainer. That is, the tongue is pulled forwardly out of the airway and the rear surfaces of the tongue and soft palate are separated with the soft palate of the user pulled away from the back wall of the pharynx.

In one desirable embodiment, a tongue depressor is provided that is adjustable in anteriorly/posteriorly (front to back) directions as well as upwardly and downwardly so that the furthest downward and backward location of the tongue rear depressor that can be tolerated by the user can more readily be located. This increases the effectiveness of tongue rear depression. Thus, a tongue rear depressor that can be easily adjusted for titrating the tongue rear depression location is desirable. If the tongue depressing portion is located too low on the user's tongue, it can irritate the tongue. If the tongue depressing portion is located too high, it is likely to be ineffective. By providing a tongue depressor with adjustable location, it is more effective to locate the tongue depressor where it is most effective without gagging the user or becoming intolerable. However, the tongue depressor can also be fixed at a desired front to rear location.

In the embodiment of FIG. 3, the illustrated tongue depressor desirably comprises a at least one tongue engager 86 with a smooth tongue contacting surface 88 of a tongue depressor portion member. The tongue depressor portion is positioned to engage a rear surface portion of the upper surface of the tongue 250. The tongue engaging portion is desirably enlarged and can, for example, comprise one or more hemispherical tongue engaging bodies, such as of acrylic or other material that will not irritate the upper surface of the tongue. The tongue engager 86 is desirably resiliently supported, such as coupled to one or more elongated arms 78. More specifically, a distal end 83 of the illustrated arm 72 can be downturned and embedded into the tongue engager 86. The main body of the illustrated arm 78 is elongated in a front to back direction and can be slidably received within a channel 309 of an arm retention slide block 310 mounted to the upper surface of the cross member or hard palate engagement portion 104 of the upper jaw coupler. The channel 309 can be sized to provide a friction fit with arm 78 to prevent sliding of the arm in a longitudinal (fore to rear or vice versa) directions while resisting such sliding in the absence of force being applied to the arm. The position of the tongue engager, in this embodiment, can be adjusted, such as by grasping and pulling on the tongue engager 86 when the tongue retainer is removed from the user's mouth. The housing 310 can be of any suitable material, such as acrylic, with the channel 309 formed therein. The channel can be formed, for example, by placing a mold element, such as a strip of rubber band of rectangular cross-section against the surface 104, forming the housing 310 and then removing the rubber band. The channel can alternatively be machined or otherwise formed in the housing 310. In the case of a channel 309 of rectangular cross-section, the arm 304 can also be of a rectangular cross-section.

The end 80 of arm 78 opposite to the distal end 83 can have an upturned or, downturned or enlarged stop portion 315 (FIG. 2) that prevents the arm from being totally removed from the tongue retainer after installation. That is, stop 315 engages housing 310 to retain the arm against removal of the arm from the appliance. The housing 310 can be reinforced, such as with stainless steel mesh, during its manufacture. As can be seen in FIG. 2, the illustrated arm 78 can have an arcuate shape that generally follows the contour of the rear surface of palate plate or engaging portion 104. The arm 78 can be positioned above or below the palate plate. The arm 78, as well as arm 70, can be of other shapes and configurations, such as rods, tubes, wires and/or more complex shapes and structures. Plural arms can also be used. Also, the arms 70, 78 can be joined together at their proximal ends. The space between the roof of the user's mouth and the palate engaging portion can accommodate the arm if positioned at this location. Moving the arm in either of the front to back or back to front longitudinal directions of arrows 314 (FIG. 2) respectively moves the arm deeper in to the user's throat or further toward the user's mouth, thereby adjusting the position of tongue engager 86 rearwardly or forwardly. To the extent the tongue engager 86 is moved rearwardly, it provides additional assistance in holding the tongue away from the airway. In addition, the arm 78 can be made of or comprise a bendable material, such as of a corrosion resistant material, with stainless steel being one specific example. As a result, the arm can be bent in downward and upward directions to shift tongue engager 86 as indicated by arrows 316 (FIG. 3) to move the tongue engager downwardly (toward the tongue) or upwardly (away from the tongue) to respectively push the tongue further away from the airway (if the tongue engager is moved downwardly in FIG. 3), or allow the tongue to encroach further into the airway (if the arm is bent upwardly in FIG. 3). Friction between the arm and the channel can be provided by the discrepancy in the curve between the elongated arm and the channel. For example, the channel 309 can be straight (e.g., with a flat upper ceiling) and the elongated arm can be curved. Alternatively, the arm can be straight and the channel can be curved to provide a discrepancy between the contours of these elements to increase the friction between these elements. As another alternative, friction can be increased by providing a roughened surface on the arm and channel. Other suitable mechanisms for preventing spontaneous motion of the tongue engager within a user's mouth can be used.

As mentioned above, the soft palate engager can be at a fixed location relative to the cross member or upper palate portion 104. Alternatively, the soft palate engager can be adjustable in anteriorly/posteriorly (front to back directions) as well as upwardly and downwardly so that the furthest upward and backward location of the soft palate engager that can be tolerated by the user can be more readily located. If the soft palate engager is located too far rearwardly, it can cause a gag reflex. If the soft palate engager is too low, it is likely to be ineffective as the distal end of the soft palate is not drawn as far away from the back wall of the pharynx. By providing a soft palate engager with an adjustable location, it can be adjusted to a location where it is most effective without gagging the user. However, the soft palate engager can be at a fixed fore/aft location relative to the palate engaging portion 104, such as by embedding an end of a soft palate engaging support arm into a portion of the soft palate engaging portion. In this case, the soft palate engager is positioned at a desired fore to aft location during manufacture.

In the embodiment of FIG. 3, the illustrated soft palate engaging assembly desirably comprises at least one soft palate engager 74 or soft palate engagement member. The soft palate engager is positioned to engage a portion of the lower surface of the soft palate 32 of the user. The soft palate engager portion 74 is desirably enlarged and can comprise one or more hemispherical tongue engaging bodies, such as of acrylic or other material that will not irritate the upper surface of the tongue. However, in a desirably example, the soft palate engager 74 is of a softer material than the tongue engager 86, at least at the soft palate engagement surface thereof in comparison to the tongue engagement surface. For example, the soft palate elevator or engager 74 can comprise a polymeric material such as rubber. Lock-free PVS (polyvinylsiloxane) is another specific example. The use of this material or another material that will not irritate the lower surface of the soft palate is selected. The soft palate engager 74 is desirably supported by a resilient support, such as by one or more elongated arms 70. More specifically, a distal end 72 of the illustrated arm 70 can be upturned and embedded into the soft palate engager 74. The main body of arm 70 is elongated in a front to back direction and can be slidably received (if not fixedly mounted in place) within a channel 309 of the arm retention block 310 mounted to the upper surface of a cross member or of a palate engaging portion 104 of the upper jaw coupler. Channel 310 can be sized to provide a frictional fit with the arm 70 to prevent sliding of the arm in a longitudinal (fore to rear) direction while resisting such sliding in the absence of force being applied to such arm, such as by grasping and pulling on the soft palate engager 74 when the appliance is removed from the user's mouth. Channel 310 can be of the same construction and formed in the same manner as the channel 309.

The proximal end 73 of arm 70 opposite to the distal end 72 can have an upturned, downturned or enlarged stop portion 319 that prevents the arm 70 from being totally removed from the appliance after installation. That is, stop 319 engages housing 310 to retain the arm 70 against removal of the arm from the appliance. As can be seen in FIG. 2, the illustrated arm 70 can have an upwardly directed arcuate shape approaching the distal end of the arm so as to be positioned to elevate a portion of the soft palate of the user rearwardly of the palate engaging portion 104 of the upper jaw coupler. The arm 70 can be mounted so as to be positioned either above or below the palate engaging portion 104, but is desirably above the arm 78 in at least one embodiment. With this arrangement, the tongue engager support arm 78 does not interfere with the upward motion of the palate engager support arm 70 and arm 70 does not interfere with the downward motion of arm 78. The space between the roof of the user's mouth and the palate engaging portion 104 can also accommodate the arm 70 if positioned at this location. If arm 70 is not fixed against longitudinal movement relative to support 104, the arm can be moved in either of the front to back or back to front longitudinal directions of arrows 321 in FIG. 2. The soft palate engager 74 in this embodiment can be moved deeper into the user's throat or further toward the user's mouth, thereby adjusting the position of the soft palate engager 74 rearwardly or forwardly. To the extend the soft palate engager 74 is moved, it can be positioned to enhance the effectiveness of drawing the distal end into the soft palate away from the rear wall of the pharynx. However, if in a fixed position relative to palate engaging portion 104, the position can be selected during manufacture for the user's anatomy to position the soft palate engager 74 in the desired location. As in the case of the arm 78, the arm 70 can also be made of or comprise a bendable material, such as of a corrosion resistant material, with stainless steel being a specific example. As a result, the arm can be bent in downward and upward directions indicated by arrows 325 in FIG. 3 to move the soft palate engager upwardly to push the soft palate further away from the tongue and draw the distal end of the soft palate further away from the back wall of the pharynx, or in the opposite direction. The soft palate engager can thereby be positioned at a location that provides comfort to the user. Friction between the arm and the channel 310 can be provided in the same manner as friction is provided between the tongue depressor arm 78 and the channel 309. Other suitable mechanisms for preventing spontaneous motion of the soft palate engager in an example of a soft palate engager movable in front to rear directions can also be used.

Figure 5A:
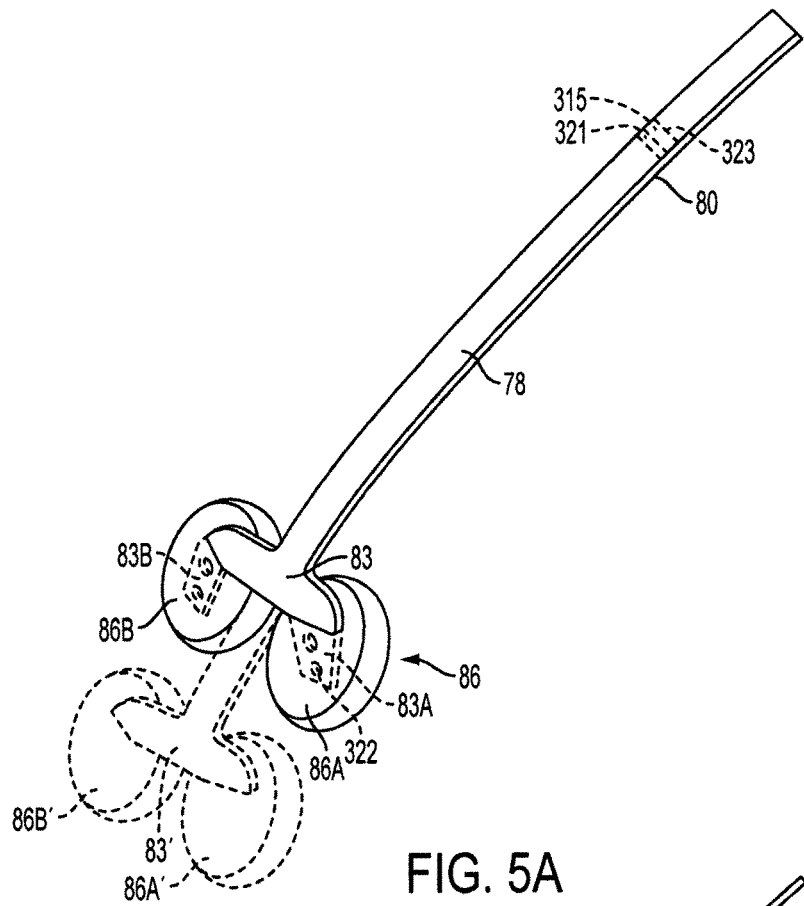
FIG. 5A illustrates one form of tongue depressor comprising an elongated tongue depressor support arm with enlarged tongue engagers affixed to a distal end portion of the tongue depressor support arm.
Figure 5B:
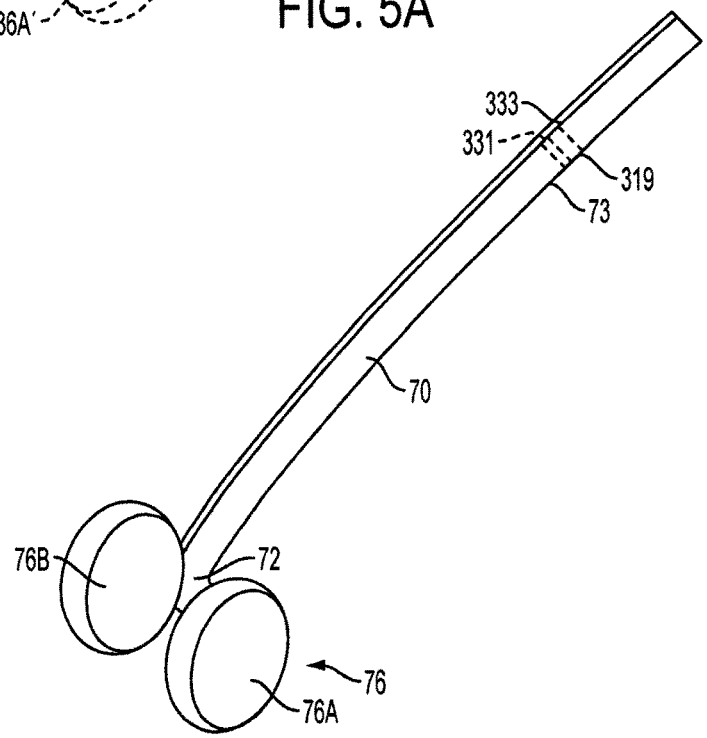
FIG. 5B illustrates one form of a soft palate engager or elevator comprising an elongated soft palate engager support arm with enlarged tongue engagers affixed to a distal end portion of the soft palate engager support arm.

With reference to FIGS. 5A and 5B, embodiments of a tongue depressor 300 and of a soft palate engager 301 are shown. In these figures, the same numbers have been used for like components discussed above in connection with FIGS. 2 and 3 and hence will not be discussed further. In FIG. 5A, the stop 315 can be formed by bending the arm 78 at location 321 to extend upwardly and then cutting the arm at location 323. The arm can be cut to a desired length for a particular individual user (e.g., a user with a large mouth can utilize a longer arm whereas a user with a smaller mouth can be fitted with a device having a shorter arm). In the embodiment of FIG. 5A, the distal end portion 83 of arm 78 is bifurcated and comprises first and second downwardly extending distal end portions 83A, 83B having openings (one being indicated by the number 322) therein. These distal end portions 83A, 83B can be inserted into the top of tongue engagers 86A, 86B (if two such spaced apart tongue engagers are used for engager 86 of FIG. 2) and adhesively or otherwise secured in place. The openings 322 provide space for additional adhesive bonding connections. Alternatively, the tongue engagers 86A, 86B can be molded around the distal end portions 83A, 83B and cured. In the case of a user with a long tongue, the engager 86 can comprise additional spaced apart engagers such as additional engagers 86A' and 86B' shown in dashed lines in FIG. 5A coupled to a distally extending end portion 83' of arm 78'.

The tongue tissue contacting surface 83 can comprise two or more tongue engagers such as tongue engagers 86A, 86B in FIG. 5A. These tongue engagers can each be of a smooth shape, such as of a polymer or plastic material with acrylic hemispheres known as cabochons being one example. Such elements are available from plastic supply companies such as TAP Plastics. In one desirable form, the diameter of the cabochons is preferably three-eighth inch or one-half inch. Acrylic spheres can also be used, although the use of hemispheres with flat portions effacing one another allow the respective support arms of the soft palate and tongue engaging elements to approach and become very close together during swallowing when the upward forces from the rear of the tongue and inward forces from the pharyngeal constrictor muscles pushes them toward each other. Other alternative shapes can also be used for the soft palate engager, as well as for the tongue engager.

The engagers 86A, 86B in this example are spaced apart and positioned to contact the tongue on opposite sides of the mid-line of the tongue. The spacing is desirably small enough that it is not filled by, or resists filling by, tissues of the engaged area. This arrangement is advantageous because it is conducive to establishing an airway passage in the middle of the tongue where there is a natural groove between the muscle masses on both sides of the tongue. For example, the space between the hemispheres can, in one example, be no more than the radius or transverse dimension of the tongue engagers. Another example of a suitable spacing between two tongue engagers would be about ⅜" to ½", or less. Such a small space between the two hemispheres, (e.g., the tapered space between adjacent surfaces of the hemispheres that diverge from one another moving away from the tongue) is not easily occluded by soft tissue of the tongue and therefore assists in maintaining a midline airway through the user's throat.

The focus on a midline airway is desirable for several reasons. First, the anatomy of the area facilitates the formation of a midline airway in the event of blockage. Second, the use of a midline airway passage avoids the very mobile tissues on the lateral portions of the airway, especially the palatopharyngeal and palatoglossal pillars and the loose tissue between them from also being sucked into the area between the rear portion of the tongue and back wall of the pharynx.

In the illustrated embodiment, the arm 78 can be comprised of a unitary elongated panel of a durable corrosion resistant material, such as stainless steel shim stock, full hardness (stainless steel stock with a thickness of 0.02 inch being one specific example). The stop 315 can be produced with a bending tool after the arm 78 has been inserted through the channel 309 from the rear to the front of the channel. The stop prevents the arm from sliding completely through the channel so that detachment of the tongue arm and tongue engager from the tongue retainer is prevented.

As shown in FIG. 1, the arms 70, 78 can have the respective distal ends 73, 83 embedded in the palatal portion 104 of the upper jaw coupler of the appliance with the distal ends of these arms terminating in the respective tissue contacting elements. The arms can be comprised of elongated strips of stainless steel having a width of from about 0.1 inch to about 0.3 inch. Desirably, arm 78 offers a greater resistance to bending than arm 70. For example, arm 78 can be comprised of an elongated strip of flat stainless steel of a thickness of approximately 0.02 inch. In contrast, arm 70 can be comprised of an elongated strip of flat stainless steel of a thickness of about 0.01 inch. Thus, arm 70 is roughly twice as flexible as arm 78. In the example where the ends of the arms are embedded into the cross member 104, the arms can have retentive features such as holes or slots therethrough that are filled with acrylic during manufacture of the cross member and upper jaw coupler to facilitate secure attachment of these arms to the cross member so they cannot break loose and pose a choking hazard. Arms of stainless steel can be easily bent, such as with three-prong pliers commonly used by dentists and orthodontists, to change the bias applied by the tissue of contacting surfaces.

Alternative shapes and materials can be used for the arms. However, the construction must be made in a manner that does not present a danger of the tissue contacting elements breaking free and being aspirated by a sleeping user. As an alternative example, the tissue contacting portion can be a plastic shape which is integral with a plastic flexible arm. The plastic flexible arm can be heated, bent to a desired shape, and then cooled to retain the arm in the desired shape.

The soft palate engager 74 in one form can comprise a single element positioned in the middle of the soft palate. The soft palate engager can be a variety of shapes. In the embodiment of FIG. 2, the soft palate engager 74 has a flat bottom facing the tongue and a rounded upper surface. The rounded upper surface can comprise an upwardly facing tissue contacting surface comprised of a generally soft material so that it can elevate the middle of the soft palate (especially if a single element is used abutting the middle of the soft palate, without applying excessive pressure on any single area of the soft palate. The upward force on the soft palate displaces the soft palate significantly in a superior direction and thereby serves to pull the distal end of the soft palate upwardly and away from (closer to the user's mouth) the location where it can be pulled or sucked into the space between the rear of the tongue and the back wall of the pharynx. Generally the force required to displace the middle of the soft palate from one fourth to one half inches, a range of displacement that has proven satisfactory when the muscles of the soft palate are at rest, is typically less than about one hundred grams. Thus, the force need not be excessive.

Figure 15:
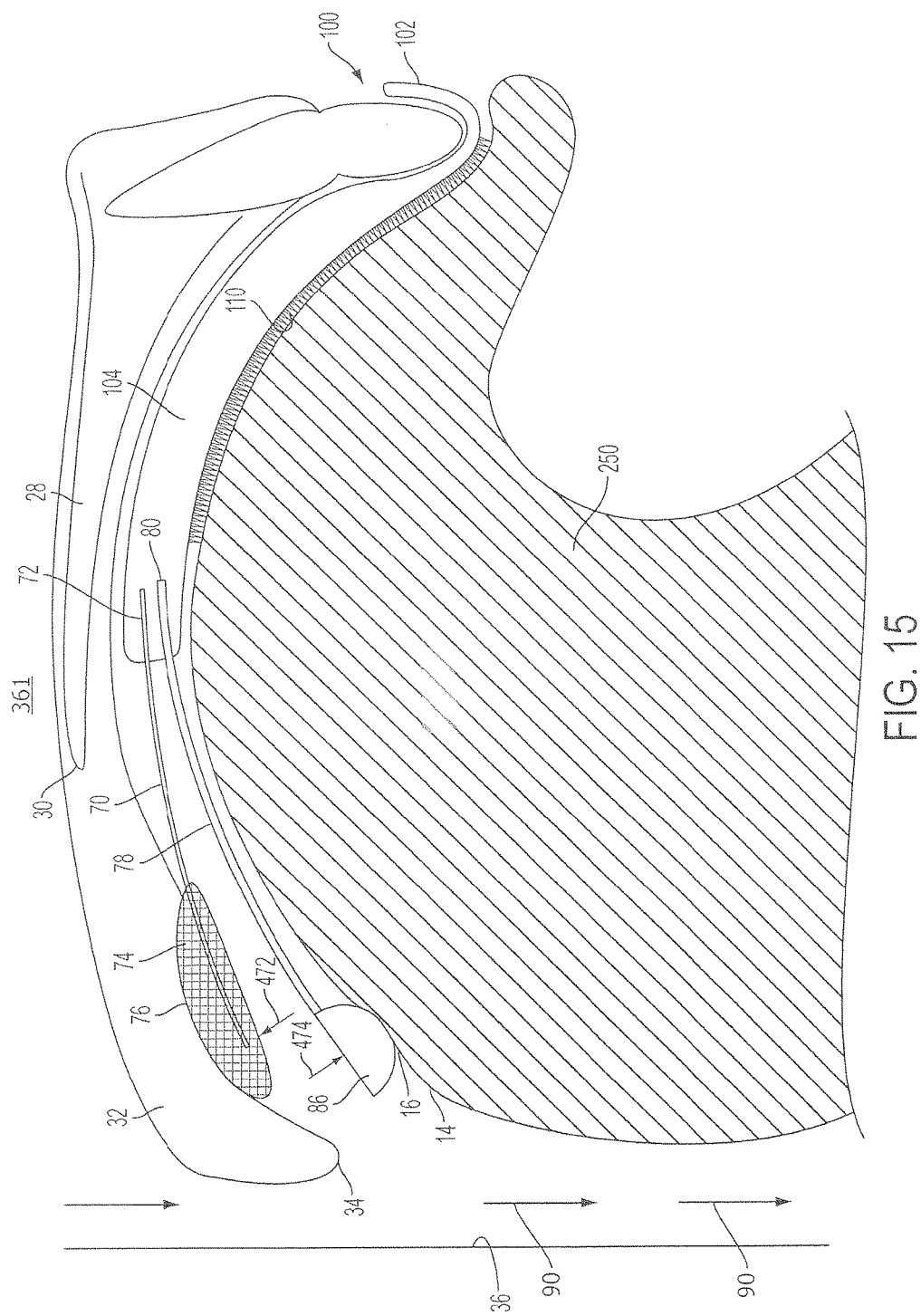
FIGS. 15-19 illustrate alternative embodiments of an upper portion of an appliance with a rear tongue depressor and soft palate elevator shown coupled to a support or cross member portion of an upper jaw coupler, and with exemplary upper tongue gripping surfaces.

If a soft palate tissue engager 74 having a flat lower surface is used, the surface accommodates the contraction of the palate muscles and strong upward and backward force produced at the rear of the tongue during swallowing. That is, clearance is provided for movement of the tongue and tongue retainer upwardly. A paddle shaped soft palate engager with a flat lower surface is one specific form, with an example thereof being shown in FIG. 15 and discussed below. In the example of FIG. 15, the tissue contacting surface area of the soft palate engager is desirably greater than the tissue contacting surface area of the tongue engager. As previously mentioned, the soft palate engager can comprise or be covered with a soft material, such as foam rubber, with a foam rubber pouch being one example. The material can be like the foam utilized for windscreens or microphones, although other soft materials can be used. In FIG. 2, the soft palate engager contacting surface 76 is shown slightly elevating the middle of the soft palate 32, resulting in pulling the distal end of the soft palate forwardly and upwardly relative to the user's mouth.

Figure 8:
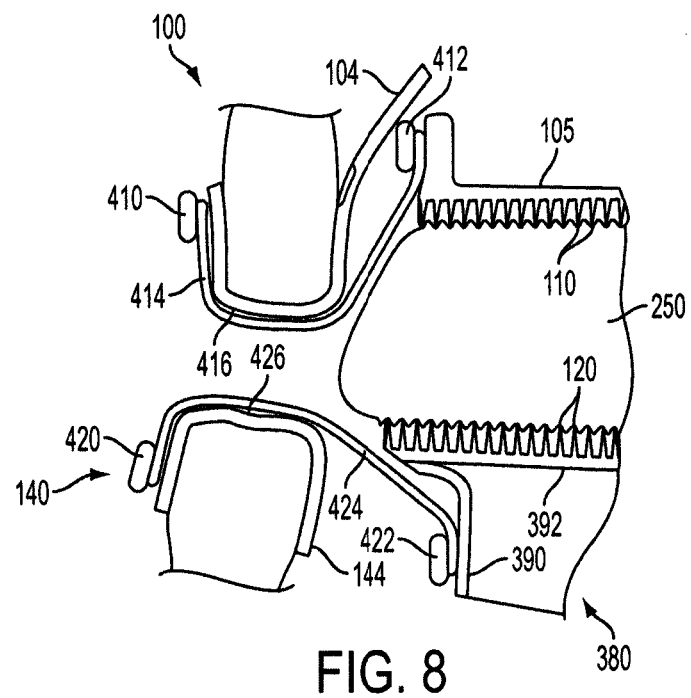
FIG. 8 is a vertical sectional view through a portion of an embodiment of a multi-level appliance for maintaining a pharyngeal airway, illustrating one exemplary biasing mechanism that can be used to couple rear portions of respective upper and lower tongue gripping surface supports to their associated jaw couplers, with a portion of a cross member of the upper jaw coupler also being shown in FIG. 8.

Although different biasing elements can be used, in the illustrated embodiment of FIGS. 8 and 9, projections such as a button 410 at the buccal side of a rear portion of the jaw coupler 102 and a button 412 at the outer side of upper support 105 are provided. An elastic band 414 extends from button 410 at the buccal side of the upper jaw coupler, across the biting surface 416 of the jaw coupler and to the button 412. This provides a downward biasing force to the upper jaw coupler upper support surface 105 at a rear portion thereof. In addition, a projection, such as a button 420, extends outwardly from the buccal side of a rear portion of the lower jaw coupler 142 and a projection, such as a button 422, extends outwardly from the outer surface of the flange 390 of lower support 380. An elastic band 424 extends from button 420, across the biting surface 426 of the lower jaw coupler and to the button 422 to provide an upward force to the lower support 380 to urge the rear end of the lower support against the user's tongue. Like projections and biasing elements can desirably be provided at the opposite side of the tongue retainer in this embodiment for coupling the upper support to the upper jaw coupler and the lower support 380 to the lower jaw coupler 140.

It should again be noted that other biasing elements and biasing element positions can be used. Also, in the case of a lower support fixed to the lower jaw coupler, the lower biasing element at the rear of the coupler can be eliminated.

In the embodiments of FIGS. 2, 3, 4 and 8, the upper tongue gripping surface 110 desirably comprise gripping elements that are continually biased downwardly onto the top (dorsal) surface of the tongue by the biasing elements. The tongue depressor 300 can be mounted to the upper support 105. However, more desirably the tongue depressor and soft palate engager are mounted to the cross member or upper palate engaging portion 104 of the upper jaw coupler, the cross member 104 being held at a fixed position relative to the user's upper jaw in an exemplary construction. The tongue depressor 300 extends rearwardly and downwardly from the rearmost end of the palate engaging portion 104 to a position to hold down the rear portion of a tongue to minimize the possibility of the rear of the tongue making contact with the soft palate and closing off the airway. In addition, the soft palate engager extends rearwardly and desirably upwardly from the palate engaging portion or cross member 84 to position the distal end of the soft palate away from the pharyngeal wall.

In another embodiment of a rear tongue depressor, the arm and adjacent surface of the palate engaging portion 104 can be provided with interfitting features, such as projections and grooves. The tongue depressor support arm in this example is movable in front or rear directions from one position following disengagement from an interfitting feature to another position. A different interfitting feature can be used to retain the arm in the fore-aft position to which it has been moved.

To bias the upper tongue gripping surface or upper support 105 away from an arch plate portion 104 of the upper jaw coupler, the biasing member, such as rubber bands, can pass from one side of the upper jaw coupler to the other side of the upper jaw coupler and across the upper surface of support 105 to urge the tongue gripping elements 110 against the tongue. In an embodiment utilizing a tether 360, the biasing member can extend, for example, from one hook of one tube and rod member or another anchoring location at one side of the appliance, across the top of the support 105 between the tether and upper surface of the tongue gripping element support 105, and to the hook of the other tube and rod mechanism or another anchoring location at the opposite side of the appliance.

The various components, such as the upper and lower supports can be made of a material such as dental acrylic to facilitate attachment to devices such as lingual buttons and mesh by embedding these components into the acrylic.

The illustrated tethers can be of any suitable material, such as one or more rectangular pieces of polymer meshes, with polyester mesh being a specific example. Stainless steel mesh is also suitable, as are other types of mesh, wire, loops or other flexible durable tethers, such as of materials used in orthodontics.

In one specific approach, the upper tether 360 (FIG. 2) can be embedded into acrylic on the front facing surface of a respective upper jaw coupler 102. Also, a lower tether 382, if used, can be embedded in the front facing surface of the lower jaw coupler 140. The portion of the tether between the attachment of the tether to the front of the upper jaw coupler and its attachment to the upper surface of the upper support 105 at a position (e.g., position 364) rearwardly of the front edge of the upper support, is an area of the tether that remains free to move. The tether is desirably of a material that can flex or move to accommodate different tongue sizes or shapes and to move slightly with the tongue during swallowing. Desirably the tether is not of a significantly stretchable material. The tethers can be provided with a mechanism to adjust their length, such as by rolling up a portion of the tether.

In one desirable embodiment, the unembedded (free) length of a tether (if used) between the lower tongue gripping surface and the front of the lower dental appliance is relatively short (for example, ¼ to ½ inch). The rear portion of the tether can be attached to the underside of the front portion of the lower tongue gripping surface support. In comparison, the unembedded (free) length of mesh between the attachment of a first end of the upper tether to a front portion of the upper jaw coupler and a second end of the upper tether to the upper support 105 is desirably longer (e.g., ¾ to 1½ inch). This is because the second end of the upper tether is desirably attached to a middle or rear portion of the upper tongue gripping surface support. The relatively longer length of the free portion of the upper tether allows the entire upper tongue gripping surface to lower with the tongue and lower jaw bone during partial opening of the mouth. During such partial opening, the tether is in effect a pivot and rotates the upper tongue gripping surface around its attachment to the front of the upper jaw coupler. Desirably, when the mouth is open so wide that the tether is nearly vertically oriented, the pull on the tether on the underside of the upper tongue gripping surface is sufficient to separate the descending tongue from the upper tongue gripping surface. At this same wide opening of the user's mouth, the bias of rubber bands (in an embodiment with such bands) that otherwise would push the upper tongue gripping surface down and away from the upper dental appliance against the tongue substantially ceases.

As another embodiment, the biasing can be provided by a compression spring positioned to urge the upper tongue gripping surface away from a palate plate of an upper jaw coupler and against the surface of the tongue. For example, one end portion of a spring can be embedded in or otherwise secured to the underside (palate facing side) of the upper support at a location opposed to the upper tongue gripping surface with the opposite end of the spring secured to a palate or arch plate. An exemplary spring can be of a relatively large diameter ½ to ¾ inch) and ⅛ to ¼ inch long. Such a spring can be made of small diameter (e.g., 0.012-0.018 inch) thick stainless steel wire or other suitable material. A single large diameter spring provides flexibility as well as positional stability for the upper tongue grasping surface. But it is to be understood that multiple smaller diameter springs, such as three ¼ inch diameter springs can be used. In connection with the lower tether, desirably the length of the free portion of the mesh is at least ⅛ inch between the portion of the mesh that is embedded in the lower support and the lower support and the portion of the mesh that is embedded in the lower jaw coupler. In addition, desirably there is a gap of at least ½ inch of free mesh or tether between the end of the mesh that is embedded in the front of the upper jaw coupler and the rearmost end of the mesh that is embedded in a portion of the upper tongue gripping surface support.

Figure 10:
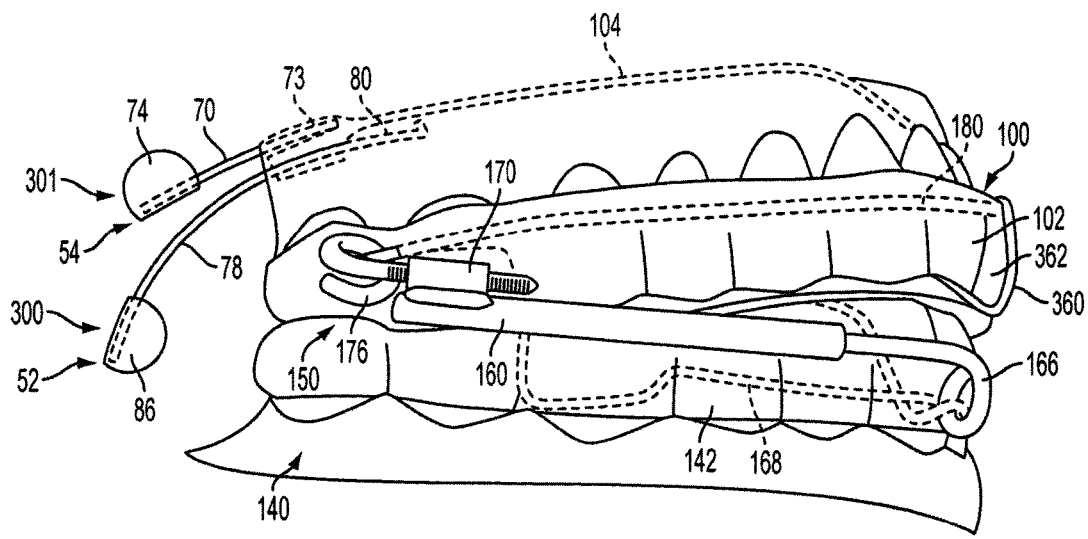
FIG. 10 illustrates another form of a multi-level appliance comprising an upper tongue gripping surface support pivoted to an upper jaw coupler, a lower tongue gripping support fixed to a lower jaw coupler, a tongue depressor and soft palate engager.
Figure 11:
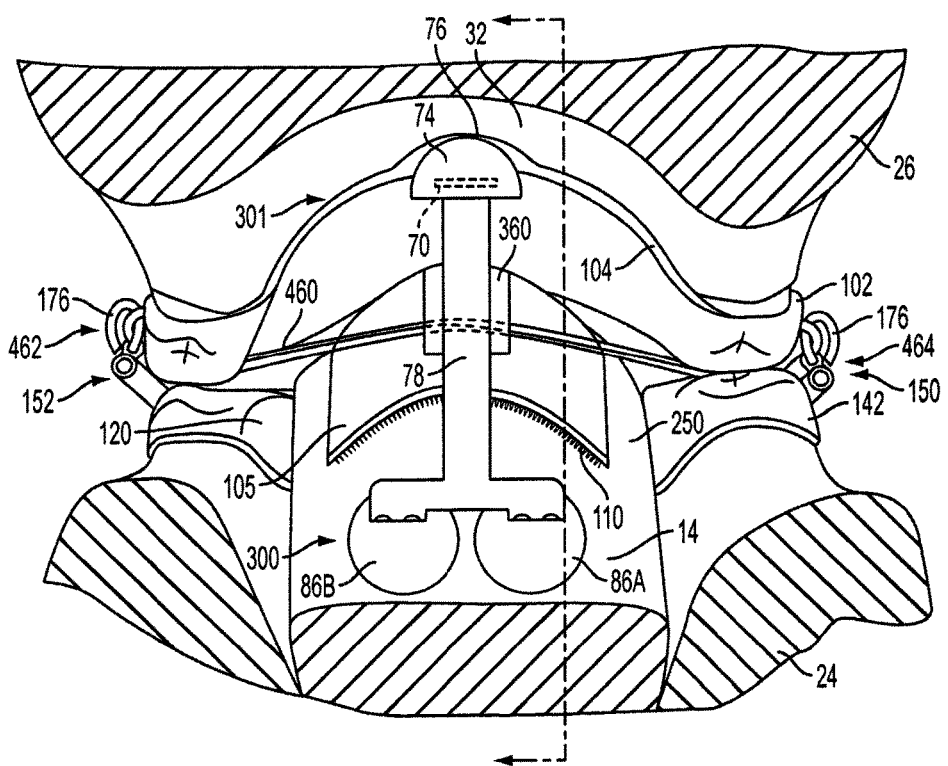
FIG. 11 is a view of the appliance of FIG. 10 looking from the rear of a user's mouth, and also showing an exemplary form of soft palate engager and tongue depressor.
Figure 12:
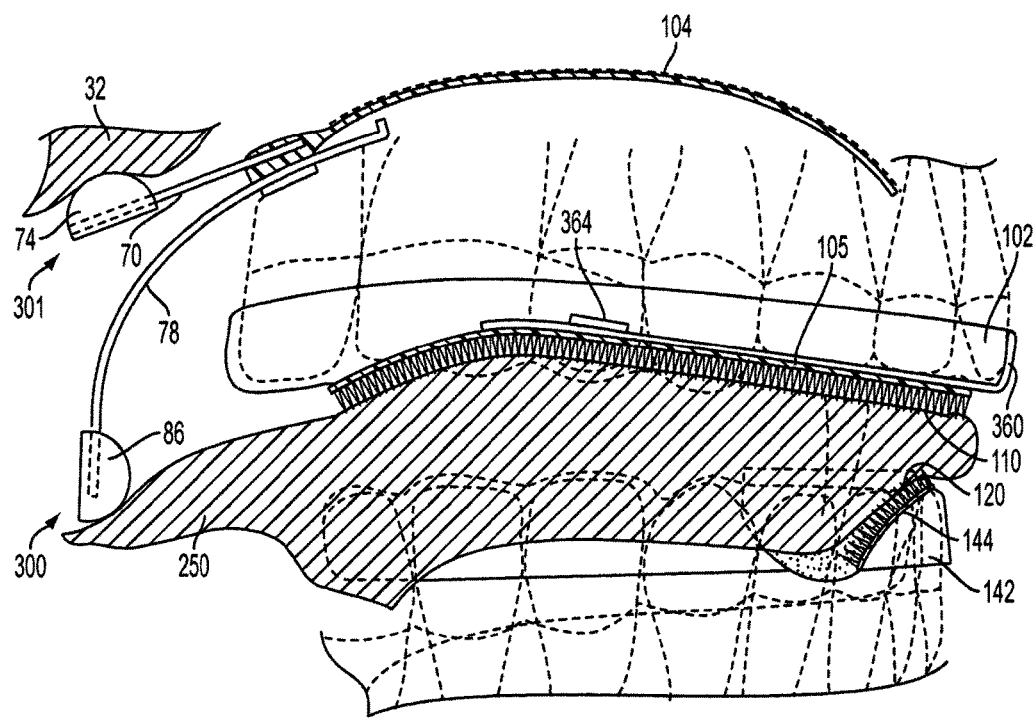
FIG. 12 is a vertical sectional side elevational view through a portion of the embodiment of FIG. 11, shown positioned in a user's mouth.
Figure 13:
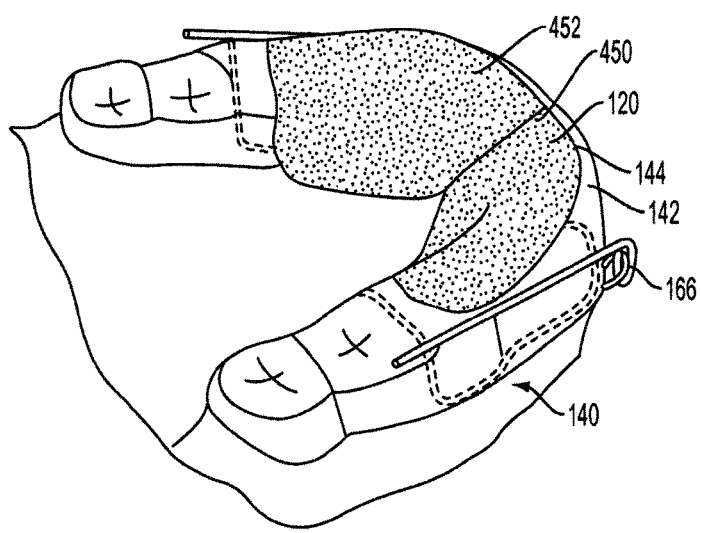
FIG. 13 is a perspective view of an exemplary lower jaw coupler and gripping surface support usable in the embodiment of FIG. 11.

FIGS. 10-14 illustrate a further embodiment of a tongue retainer with a rear tongue portion depressor and soft palate engager. In FIG. 10, the soft palate and user's tongue are not shown for convenience. Components like those previously discussed have been assigned the same numbers in these figures and will not be discussed in detail. In the embodiment of these figures, the lower jaw coupler 142 is shown on the lower jaw of a user. The lower tongue gripping element support 144 (FIG. 14) comprises a body having a gripping surface thereon with upwardly facing tongue gripping projections that some or all of which can be angled forwardly toward the tip of the tongue. As best seen in FIG. 13, the support 144 and lower tongue gripping projections 120 can comprise first and second tongue gripping components 450, 452. The components 450, 452 are shown positioned forwardly on the lower jaw coupler 142 in a generally U shaped configuration adjacent to the filiform papillae of the lower surface of the tongue for engaging the tongue when the tongue retainer is in position and the mouth is closed. The lower support 144 can be fixed to the lower jaw coupler with the lower jaw coupler mounted to the teeth of the user. Alternatively, a floating or pivoted lower jaw support 380, such as shown in FIG. 8, can be used. In the example of FIGS. 10-14, the lower support 144 is desirably not tethered to the lower jaw coupler as it is fixed in place on the lower jaw coupler. The positioning of the tongue gripping elements 120 against the tongue, the tongue depressing element 86 against the tongue, and the soft palate engaging element 74 against the soft palate when the mouth is closed is shown in FIG. 12.

As can be seen in FIGS. 10 and 11, the illustrated tongue retainer can comprise tube and rod mechanisms 150, 152 for coupling the upper and lower jaw couplers together, such as in the manner shown in FIG. 2. The upper jaw coupler 102 in this example comprises a palate plate or palate plate engaging portion 104 desirably positioned to engage the lower surface of the upper palate of the user and interconnect the teeth engaging portions 102 of the upper jaw coupler. The dashed lines in FIG. 15 show reinforcing wires that can be embedded in the material that comprises the respective upper and lower jaw couplers.

Figure 14:
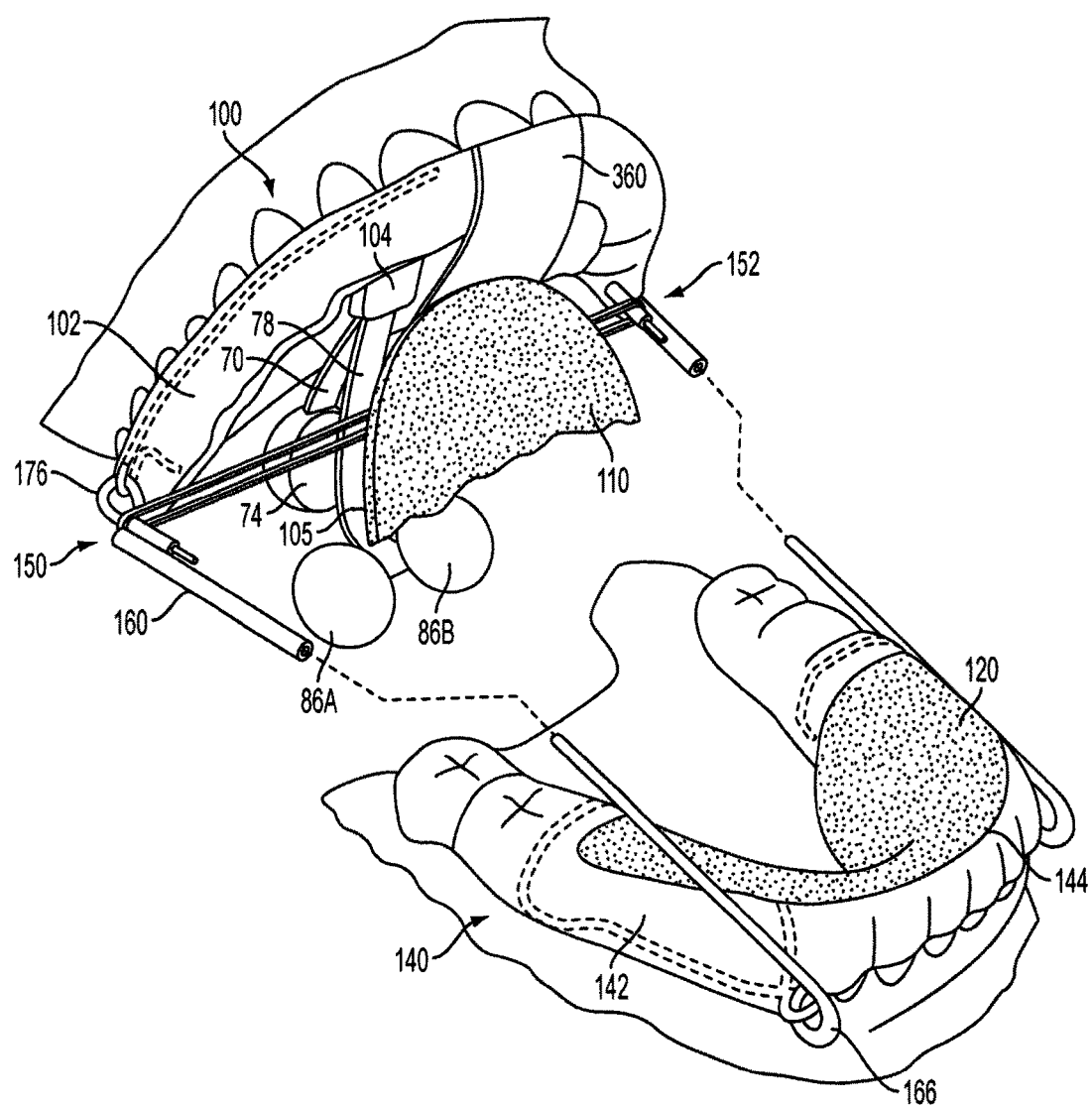
FIG. 14 is a perspective view of the appliance of the form shown in FIG. 11, with upper and lower components of the appliance shown separated from one another for convenience in illustrating these components.

A rearwardly and downwardly extending tongue depressor assembly 300 and soft palate engaging assembly 301 are also shown in the embodiment of FIGS. 10-14, as is best seen in FIGS. 11, 12 and 14. The illustrated tongue depressor comprises an arm 78 having a distal end portion supporting first and second hemispherical or otherwise shaped tongue engagers 86A, 86B (FIG. 11). The arm 78 in this embodiment is slidably received through a channel provided in an arm receiving housing (not visible in these figures) mounted to the palate engaging portion 104. The illustrated soft palate engager comprises an arm 70 having a distal end portion supporting a hemispherical (which can comprise a flattened hemispherical, ovoid or otherwise shaped) soft palate engager 74 having a surface 76 positioned to engage the soft palate of the user. The arm 70 is shown fixed to the palate engaging portion 104. A biasing member, that can comprise a single rubber band 460, engages and pushes down on the upper surface of upper tongue gripping element support 105. The outer ends of the band 460 can be looped around outwardly projecting portions of the respective tube and rod mechanisms (e.g., portions 176) with the tube and rod mechanisms holding the outwardly positioned ends of the band in place. Thus, as can be seen in FIG. 11, the illustrated band 460 can extend from the tube and rod component 176 at a location along the rear buccal surface of the jaw coupler 102 at side 462 of the jaw coupler, across the lower biting surface at such side of the jaw coupler, into engagement with the upper surface of element 105 (and underneath a tether 360 in this example), across the biting surface of the jaw coupler 102 at the opposite side 464 of the jaw coupler, and into engagement with a component of the tube and rod mechanism, such as a projecting component 176 thereof, at the buccal side 464 of the jaw coupler. Thus, the band 460 is coupled to the respective sides of the jaw coupler at a rearward location of the jaw coupler in this example.

In the embodiment of FIGS. 10-14, desirably no biasing members interconnect the upper jaw coupler to the lower jaw coupler. In addition, desirably in this embodiment, the only biasing member comprises one or more downward force-applying members coupling a rear portion of the upper support to the respective sides of the upper jaw coupler. Thus, intra-arch biasing is desirably provided in this embodiment, with only the upper support being biased. Of course, additional biasing elements can be used in the embodiments of FIGS. 10-14, but this would be less desirable.

The tether 360 operates in the same manner as previously described in connection with FIG. 2 to allow movement of the upper tongue gripping element support 105 with the movement of the tongue. Also, with the mouth moved to a wide open position, the tongue retainer is operable to facilitate the removal of the tongue retainer from the user's mouth.

FIGS. 15-19 illustrate additional embodiments of an upper jaw coupling assembly of an appliance. The lower jaw assemblies can be like the assemblies that have previously been described or of a different structure. Also, the teeth gripping elements of FIGS. 15-19 can alternatively be pivotally coupled to an upper jaw coupler such as previously described.

FIG. 15 illustrates an upper jaw coupler portion of an appliance comprising an upper jaw coupler 100 with a teeth coupler portion 102, tongue gripping elements 110, and a cross member or palate engaging portion 104 of the upper jaw coupler. In the embodiment of FIG. 15, the proximal end 80 of arm 78 of the illustrated rear tongue surface engager is embedded in an end portion of the cross member 104. In addition, the proximal end 72 of arm 70 carrying the soft palate engager 74 is also embedded into the cross member 104 at a location above the arm end portion 80.

Figure 16:
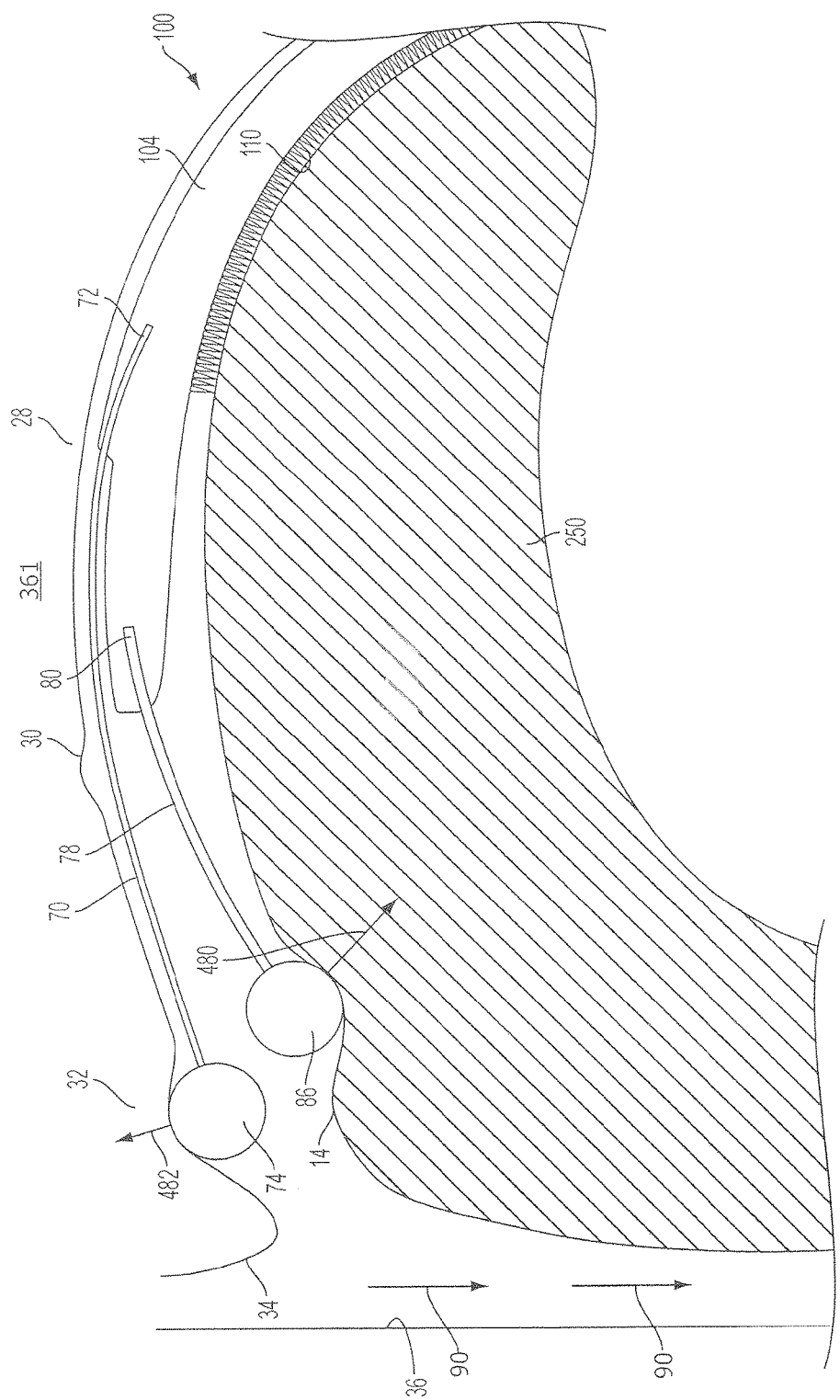

In the embodiment of FIG. 16, the lower or tongue contacting surface of tongue engagement member 83 is located more forwardly (closer to the lips of the user) than the upper soft palate tissue contacting element 74. The rear portion of the tongue has many gag reflexes. Therefore, locating the tongue engagement component that contacts the soft tissue of the rear portion of the tongue at a more forward location enhances the comfort for the user. In the embodiment of FIG. 16, the soft palate contacting element 74 is comprised of a sphere, such as of a polymer material such as acrylic. The use of a spherical body reduces the remote chance of a rough surface (such as the edge of a hemispherical body used for contacting the soft palate in FIG. 1) contacting the rear of the tongue during swallowing. Locating the spherical soft palate tissue contacting element 74 further back than the tongue contacting element 83, which also can be spherical, prevents the lower portion of the soft palate tissue from contacting the arm 78 or the tongue engaging element 83 when these contacting portions are pushed together during swallowing. During swallowing no inspiration of air occurs. Therefore, there is no need to separate the tissues of the soft palate and the rear of the tongue. Thus, allowing the arms 70, 78 to approach one another, and desirably to become close enough to make contact, during swallowing facilitates the swallowing act. The embodiment of FIG. 16 can be modified to replace the spherical tissue engaging elements 74, 83 with respective hemispherical elements that are flat along the surfaces adjacent to one another to allow a closer approach or contact of the arms 70, 78 during swallowing. In the embodiment of FIG. 16, the proximal end 80 of the arm 78 is connected at a more rearward location (relative to the user's mouth) of the palate engaging portion 104 than the location of connection of the proximal end 72 of the arm 70 to the palate engaging portion. One advantage of this offset location of the tissue supporting arms is that the bias provided by the shorter lower arm 78 has a vector which pushes forward toward the mouth of the user as well as downwardly on the rear portion of the tongue, as indicated by the arrow 480 in FIG. 16. That is, the forward portion of the vector 480 is greater than the corresponding forward portion of the vector 474 in FIG. 15. Such a forward vector of force assists in maintaining the rear of the tongue away from the back wall 36 of the retroglossalpharynx and assists in maintaining the tongue in a protrusive position. Another advantage of this arrangement is that it facilitates the use of a shorter stiffer arm 78 to provide a greater force downwardly on the firm tissues of the tongue than the force applied by a longer more resilient arm 70 (due to the more forward location of connection of proximal end 72 of arm 70 to the palate engaging portion 104) against the soft tissues of the palate. A vector 482 in FIG. 16 illustrates the lesser force against the soft tissues of the palate.

Figure 17:
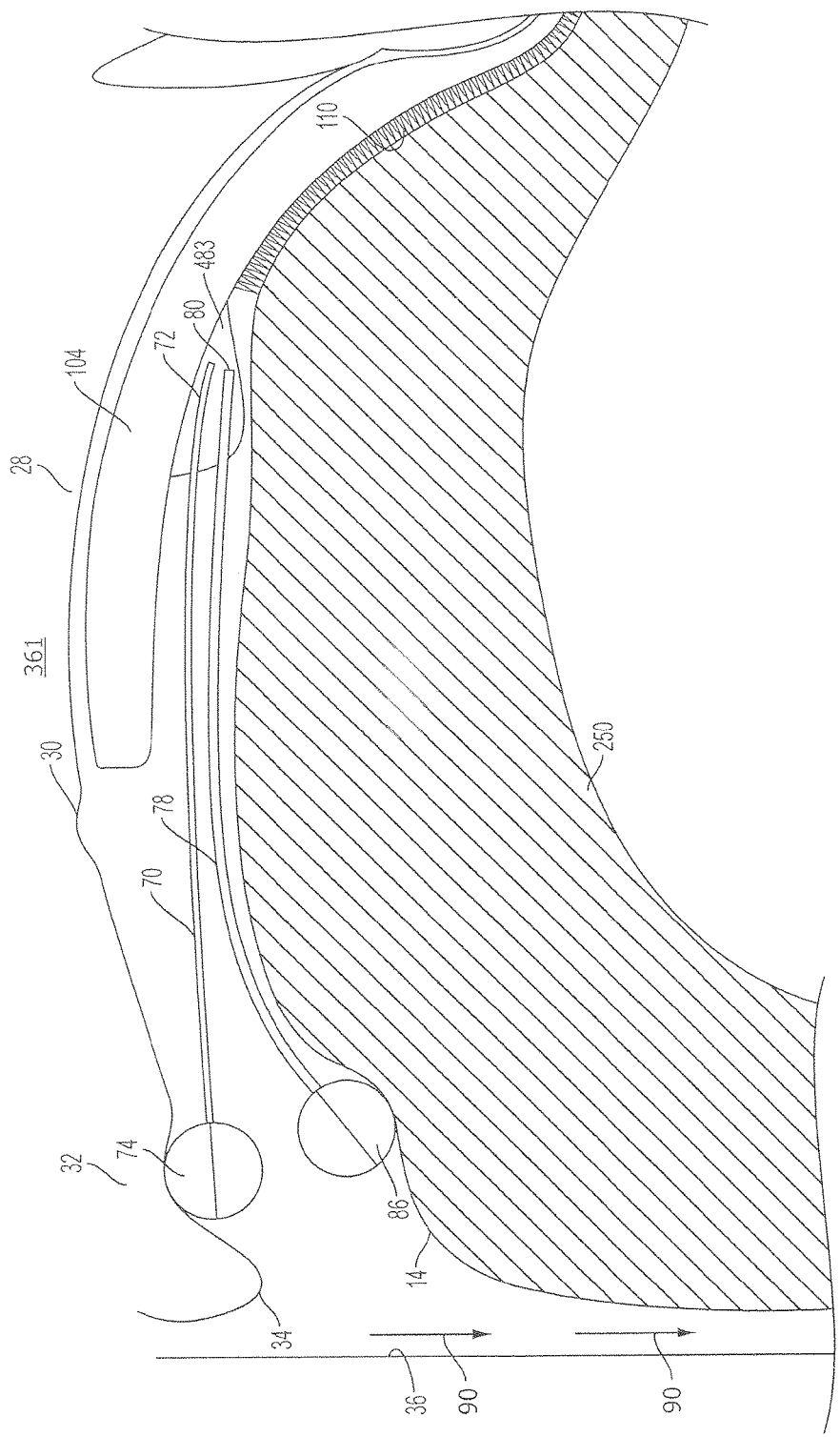

FIG. 17 illustrates an embodiment in which the respective proximal ends 72, 80 of the arms 70 and 78 are embedded in an enlarged portion 483 of the palate engaging member 104 or cross member located at the underside of the cross member. These arms 72, 80 can be mounted to an upper surface of the cross member if desired. The arms 70, 78 respectively support the soft palate engaging element 74 and tongue engaging element 83 which can be spherical, semi-spherical, or some other shape, desirably with a smooth tissue engaging surface. The elements 74 and 83 in this embodiment can comprise magnets that are of the same polarity, such that element 74 repels element 83 and vice versa. As a result, element 74 is biased away from element 83 and toward the soft palate tissue and element 83 is biased away from element 74 and toward the tissue of the tongue at a rear portion of the tongue.

Figure 18:
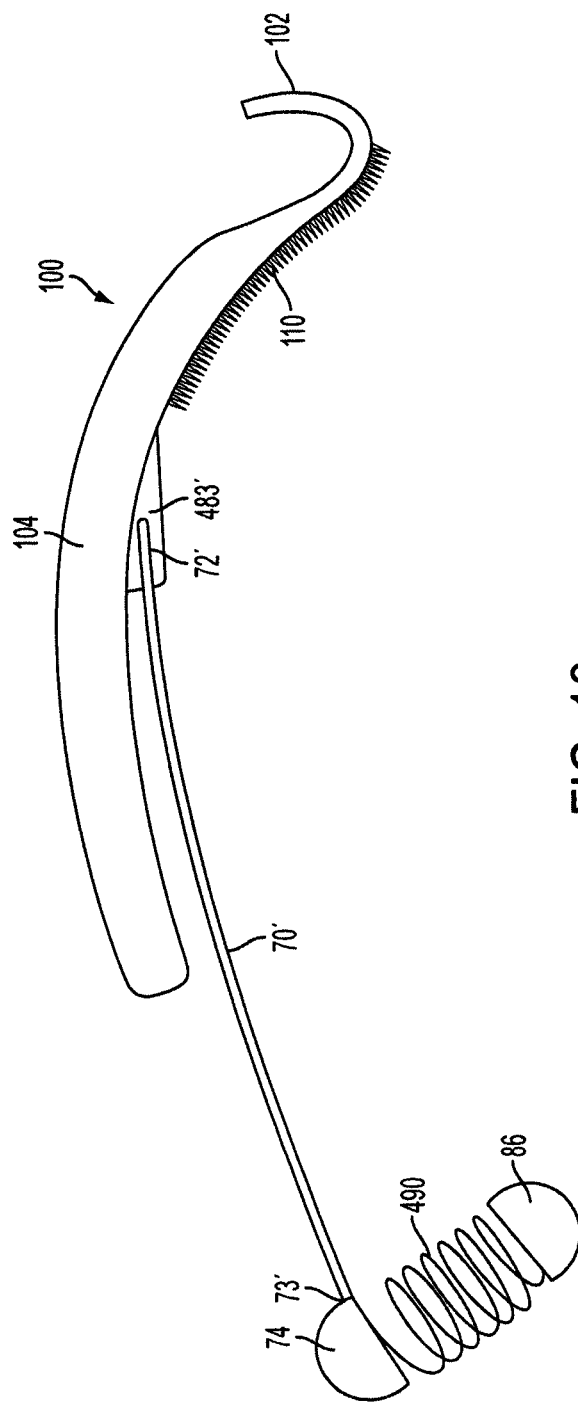

In the embodiment of FIG. 18, a single arm 70' is utilized to support the respective tissue engaging elements 74, 83. In FIG. 18, the arm 70' is shown with a proximal end portion 72' embedded within an enlarged portion 483' of the palate engaging portion or cross member 104 at the undersurface of the palate engaging portion. The arm portion 72' can be slidably coupled to the palate engaging portion, embedded in a rear end portion of the palate engaging portion, or positioned above the palate engaging portion as desired. Arm 70' has its distal end 73' coupled to a soft palate engager 74. The engager 74 can be like the previously described soft palate engagers. A spring 490 is connected to soft palate engager 74 and also to a rear tongue surface engager 83. The spring 490 urges the engaging components 74, 83 apart such that engager 74 engages the soft palate tissue and engager 83 engages the rear tongue surface tissue. This occurs because the spring 490 is sized to be compressed when positioned in the user's mouth. Alternatively, the arm 70' can be replaced by an arm 78' connected to the tongue engaging element 83 with a spring 490 connecting the element 74 to the element 83 without the use of an arm 70'. Therefore, in the example of FIG. 18, a single arm can be used to support the opposing tissue engaging elements.

Figure 19:
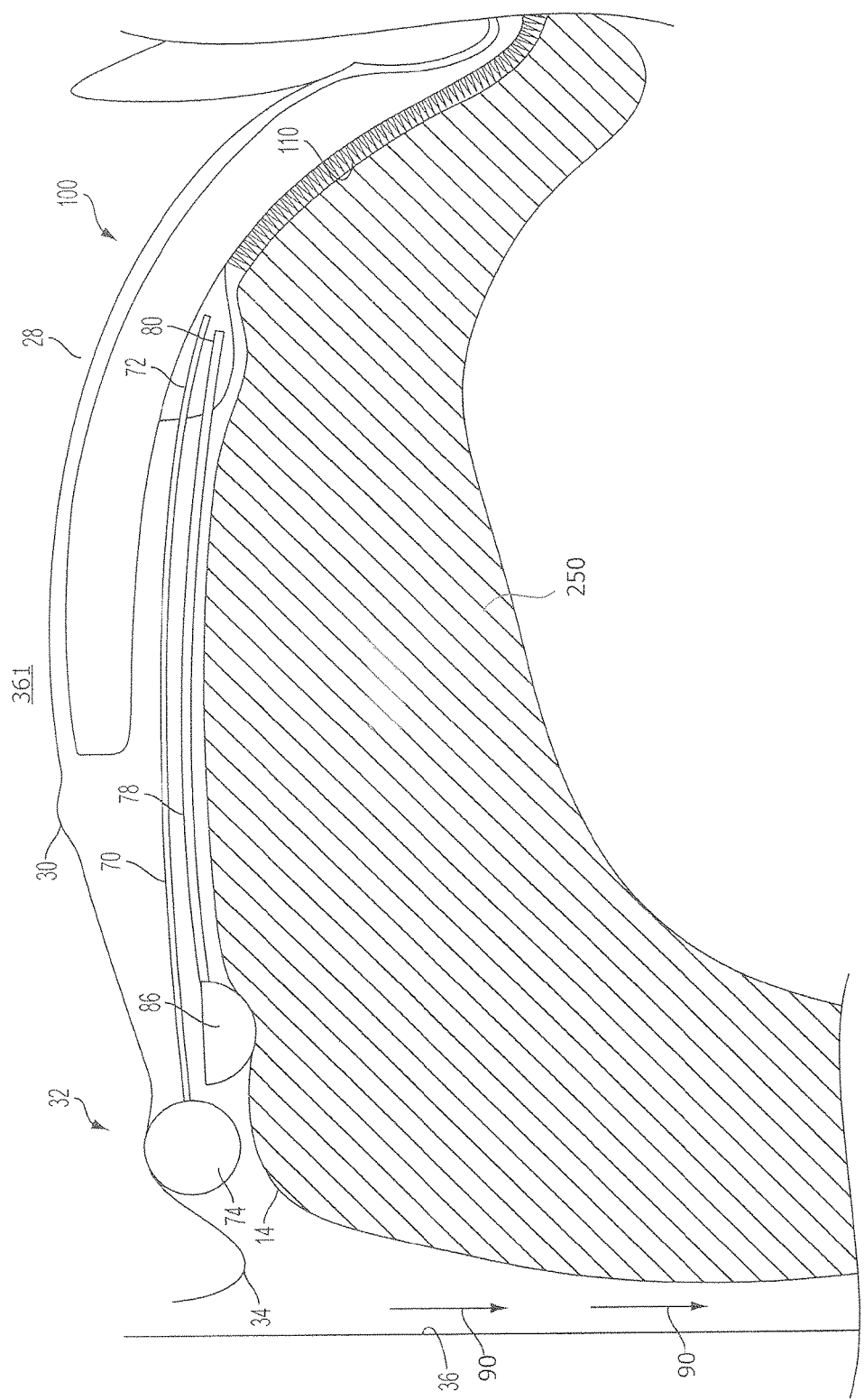

The embodiment of FIG. 19 is similar to the embodiment of FIG. 17 except that the palate engaging element 74 is supported by arm 70 at a location rearwardly (deeper into the user's mouth) than the tongue engaging element 83. In addition, the palate engaging element 74 is shown as a spherical element with both top and bottom portions. In contrast, the exemplary tongue engaging portion is of a flatter construction. During swallowing, the arm 78 can approach and come very close to the arm 70 because the flatter lower profile surface of element 83 clears the lower surface of the element 74.

In the above description, various types of biasing mechanisms can be used, in addition to, in lieu of and/or in combination with springs and resilient materials such as elastic bands, to provide biasing forces to urge one or both of the upper and lower tongue gripping surfaces together. In addition, alternative manufacturing techniques can be used to provide tongue gripping surfaces. For example, in addition to approaches previously described, small spike-like tongue gripping projections can be made by hot stamping of a plastic panel or by using miniature round punches in a metal panel. In addition, for people with pierced tongues, the source of biasing between upper and lower tongue gripping surfaces can be a bolt or other mechanical fastener which engages upper and lower tongue gripping surfaces and extends through the pierced portion of the tongue.

Having illustrated and described the principles of my invention with reference to a number of embodiments, it should be apparent of those of ordinary skill in the art that these embodiments may be modified in arrangement in detail without departing from such principles. I claim all such embodiments and modifications that fall within a scope of any one or more of the following claims.

The invention claimed is:

1. An apparatus for grasping and restraining a front portion of the tongue of a user, engaging a rear portion of the tongue of the user, and engaging the soft palate of the user rearwardly of the hard palate of the user so as to resist closing of the pharyngeal airway of the user, the apparatus comprising:

a first upper support;

the first upper support comprising an upper support body portion comprising an upper surface, a lower surface, a front, a rear, and first and second sides, the first upper support also comprising a first tongue gripping surface, the first tongue gripping surface comprising a plurality of tongue engaging projections adapted to extend from the lower surface of the upper support body portion toward the upper surface of a front portion of the tongue of a user;

an upper jaw coupler adapted to couple the first support to the upper jaw of the user, wherein the upper support body portion is pivotally coupled to the upper jaw coupler such that the front and rear of the upper support body portion are movable upwardly and downwardly relative to the upper jaw coupler, the upper jaw coupler comprising an upper cross member portion for positioning adjacent to at least a portion of the hard palate of the user;

a second lower support;

the second lower support comprising a lower support body portion comprising an upper surface, a lower surface, a front, a rear, and first and second sides, the second lower support also comprising a second tongue gripping surface, the second tongue gripping surface comprising a plurality of tongue engaging projections adapted to extend from the upper surface of the lower support body portion toward the lower surface of the front portion of the tongue of a user;

a lower jaw coupler adapted to couple the second support to the lower jaw of the user;

at least one biasing member coupled to at least one of the first and second supports and adapted to urge at least one of the first and second tongue gripping surfaces toward the other of the first and second tongue gripping surfaces with a front portion of a user's tongue positioned therebetween and adapted to grasp and restrain the tongue of the user therebetween;

a tongue depressor projecting from the upper cross member portion of the upper jaw coupler to a position rearwardly of the cross member portion and adapted to engage and depress the rear portion of the tongue of the user;

a soft palate engager projecting from the upper cross member portion of the upper jaw coupler to a position rearwardly of the cross member portion and adapted to engage a portion of the soft palate of the user rearwardly of the hard palate of the user; and wherein the tongue depressor and soft palate engager are adapted to urge the rear portion of the tongue of the user and the engaged portion of the soft palate of the user away from one another so as to resist closing of the pharyngeal airway of the user.

2. An apparatus according to claim 1 wherein the second lower support is fixed to the lower jaw coupler.

3. An apparatus according to claim 1 wherein the second lower support body portion is pivotally coupled to the lower jaw coupler such that the lower support body portion is movable upwardly and downwardly relative to the lower jaw coupler.

4. An apparatus according to claim 1 comprising a tether pivotally connecting the upper support body portion to the upper jaw coupler, the tether comprising first and second end portions, the first end portion of the tether being pivotally connected to a front portion of the upper jaw coupler, the second end portion of the tether being pivotally connected to the upper surface of the first upper support at a location that is at or rearwardly of the center of the upper support body portion.

5. An apparatus according to claim 2 comprising a tether comprising first and second end portions, the first end portion of the tether pivotally connecting the upper support body portion to a front portion of the upper jaw coupler, the second end portion of the tether is connected to the upper surface of the upper support body portion at a location that is at or rearwardly of a central portion of the upper support body portion.

6. An apparatus according to claim 1 comprising first and second telescoping mechanisms positioned along respective sides of the upper and lower jaw couplers, each of the telescoping mechanisms comprising first and second end portions and being coupled at one of the first and second end portions to one of the upper and lower jaw couplers and being coupled at the other of the first and second end portions to the other of the upper and lower jaw couplers.

7. An apparatus according to claim 4 wherein the at least one biasing mechanism is coupled to the upper jaw coupler and to the upper surface of the upper support body portion so as apply a downward biasing force to the upper surface of the upper support body portion to urge the first upper support downwardly toward the second lower support at least when the user's mouth is closed.

8. An apparatus according to claim 1 wherein the tongue depressor comprises an elongated arm with first and second tongue depressor end portions, the first tongue depressor end portion being mounted to the upper cross member portion of the upper jaw coupler, the second tongue depressor end portion being spaced rearwardly of the upper cross member portion of the upper jaw coupler, and a tongue engager with a tongue engagement surface supported by the second tongue depressor end portion and wherein the tongue depressor movable relative to the upper cross member portion at least in upward and downward directions.

9. An apparatus according to claim 1 wherein the tongue depressor is movable relative to the upper cross member portion in front to rear directions, rear to front directions, and upward and downward directions.

10. An apparatus according to claim 1 wherein the tongue depressor comprises at least one elongated tongue depressor support arm with a first tongue depressor support arm portion mounted to the upper cross member portion and a second distal tongue depressor support arm end portion spaced from the upper cross member portion, and at least one tongue engager mounted to the second distal tongue depressor support arm end portion; and wherein the soft palate engager comprises at least one elongated soft palate engager support arm with a first soft palate arm end portion mounted to the upper cross member portion and a second distal soft palate arm end portion spaced from the upper cross member portion, and at least one soft palate engager mounted to the second distal soft palate arm end portion.

11. An apparatus according to claim 10 wherein the tongue depressor support arm and the soft palate engager support arm each comprise a bendable material, wherein bending the tongue depressor support arm downwardly relative to the upper cross member portion shifts the tongue engager downwardly and bending the tongue depressor support arm upwardly relative to the upper cross member portion shifts the tongue engager upwardly, and wherein bending the soft palate engager support arm downwardly relative to the upper cross member portion shifts the soft palate engager downwardly and bending the soft palate support arm upwardly relative to the upper cross member portion shifts the tongue engager upwardly; wherein the tongue depressor support arm positions and holds the tongue engager at different upward and downward positions depending upon the bending of the tongue depressor support arm; and wherein the soft palate engager support arm positions and holds the soft palate engager at different upward and downward positions depending upon the bending of the soft palate engager support arm.

12. An apparatus according to claim 1 wherein the soft palate engager is coupled to the upper cross member portion and is movable relative to the upper cross member portion at least in upward and downward directions.

13. An apparatus according to claim 1 wherein the soft palate engager is coupled to the upper cross member portion and is movable relative to the upper cross member portion in front to rear directions, rear to front directions, and upward and downward directions.

14. An apparatus according to claim 1 wherein the tongue depressor is movable relative to the upper cross member portion in front to rear directions, rear to front directions, and upward and downward directions, and wherein the soft palate engager is movable relative to the upper cross member portion at least in upward and downward directions.

15. An apparatus according to claim 1 wherein the tongue depressor comprises at least one of resilient band supports, a spring, and magnets operable to bias the tongue depressor away from the soft palate engager.

16. An apparatus according to claim 1 wherein the tongue depressor comprises a tongue engager and a bendable tongue depressor mount mounting the tongue depressor to the upper cross member portion and that positions the tongue engager rearwardly of the upper crossmember portion; and wherein the soft palate engager comprises a soft palate engager and a bendable soft palate engager mount mounting the soft palate engager to the upper cross member portion and that positions the soft palate engager rearwardly of the upper cross member portion, and wherein the tongue depressor mount and soft palate engager mount being operable to permit movement of the rear of the tongue to allow closing of the pharyngeal airway during swallowing by the user.

17. An apparatus according to claim 1 wherein the tongue depressor comprises at least one tongue engager with a tongue engaging surface for engaging the rear portion of the tongue of the user, wherein the soft palate engager comprises at least one soft palate engager with a soft palate engaging surface positioned and adapted to engage the soft palate of the user at a location rearwardly of the hard palate of the user, the soft palate engaging surface being softer than the tongue engaging surface.

18. An apparatus according to claim 1 wherein the tongue depressor comprises a first tongue engager with a first tongue engaging surface and a second tongue engager with a second tongue engaging surface, the first and second tongue engaging surfaces being positioned to engage the tongue of the user on opposite sides of the center of tongue, and wherein the soft palate engager comprises one soft palate engager with a soft palate engaging surface positioned to engage the soft palate of the user at a location along the center of the soft palate.

19. An apparatus according to claim 1 wherein the upper cross member portion comprises an upper palate engaging portion of the upper jaw coupler, wherein the tongue depressor comprises at least one elongated tongue depressor support arm with a first tongue depressor support arm portion mounted to the upper palate engaging portion and a second distal tongue depressor support arm end portion spaced from the upper palate engaging portion, and at least one tongue engager mounted to the second distal tongue depressor support arm end portion; wherein the tongue depressor support arm comprises a bendable material, wherein bending the tongue depressor support arm downwardly relative to the upper palate engaging portion shifts the tongue engager downwardly and bending the tongue depressor support arm upwardly relative to the upper palate engaging portion shifts the tongue engager upwardly; wherein the soft palate engager comprises at least one elongated soft palate engager support arm with a first soft palate arm portion mounted to the upper palate engaging portion and a second distal soft palate arm end portion spaced from the upper palate engaging portion, and at least one soft palate engager mounted to the second distal soft palate arm end portion; wherein the soft palate engager support arm comprises a bendable material, wherein bending the soft palate engager support arm downwardly relative to the upper palate engaging portion shifts the soft palate engager downwardly and bending the soft palate support arm upwardly relative to the upper palate engaging portion shifts the soft palate engager upwardly; and wherein the bendable tongue depressor support arm and bendable soft palate engager support arm are configured and supported to bend to permit movement of the rear of the tongue to allow closing of the pharyngeal airway during swallowing by the user.

20. An apparatus according to claim 19 wherein the second lower support is fixed to the lower jaw coupler, the apparatus further comprising a tether pivotally connecting the upper support body portion to the front of the upper jaw coupler, the tether being connected to the first upper support at a location intermediate to the front and rear of the upper support body portion, wherein the at least one biasing mechanism is coupled to the upper jaw coupler and to the upper surface of the upper support body portion so as to urge the first upper support downwardly toward the second lower support at least when the user's mouth is closed, and the apparatus further comprising first and second telescoping mechanisms positioned along respective sides of the upper and lower jaw couplers, each of the telescoping mechanisms comprising first and second end portions and being coupled at one of the first and second end portions to one of the upper and lower jaw couplers and being coupled at the other of the first and second end portions to the other of the upper and lower jaw couplers.

21. An apparatus according to claim 19 wherein the tongue depressor comprises at least one tongue engager with a tongue engaging surface positioned to and adapted to engage the rear portion of the tongue of the user, wherein the soft palate engager comprises at least one soft palate engager with a soft palate engaging surface positioned to and adapted to the soft palate of the user, the soft palate engaging surface being softer than the tongue engaging surface.

22. An apparatus according to claim 19 wherein the tongue depressor comprises a first tongue engager with a first tongue engaging surface and a second tongue engager with a second tongue engaging surface, the first and second tongue engaging surfaces being positioned and adapted to engage the tongue of the user on opposite sides of the center line of the tongue, and wherein the soft palate engager comprises one soft palate engager with a soft palate engaging surface positioned to engaging the soft palate of the user at a location along the center of the soft palate.

23. An upper jaw assembly for an apparatus for grasping and restraining the tongue of a user, the tongue of the user having an upper tongue surface and a tongue rear portion, and for urging the tongue rear portion away from the soft palate of a user, the soft palate of the user extending rearwardly of the hard palate of the user, the upper jaw assembly comprising:
 a first upper support;
 the first upper support comprising an upper support body portion comprising an upper surface, a lower surface, a front, a rear, and first and second sides, the first upper support also comprising a first tongue gripping surface, the first tongue gripping surface comprising a plurality of tongue engaging projections that are adapted to extend from the lower surface of the upper support body portion toward the upper surface of the front portion of the tongue of a user;
 an upper jaw coupler adapted to couple the first support to the upper jaw of the user, the upper jaw coupler comprising a cross portion spanning the users mouth from one side thereof to the other, wherein the upper support body portion is pivotally coupled to the upper jaw coupler such that the front and rear of the upper support body portion are movable upwardly and downwardly relative to the upper jaw coupler;

a tongue depressor coupled to the cross portion and projecting rearwardly and downwardly from the cross portion and to a position rearwardly of the upper jaw coupler and adapted to engage the tongue rear portion, wherein the tongue depressor is movable relative to the cross portion in upward and downward directions; and a soft palate engager coupled to the cross portion and projecting at least rearwardly from the cross portion and to a position rearwardly of the upper jaw coupler and adapted to engage the soft palate of the user rearwardly of the hard palate of the user, wherein the soft palate engager is movable relative to the cross portion in upward and downward directions.

24. An apparatus according to claim 23 comprising a tether pivotally connecting the upper support body portion to the front of the upper jaw coupler, the tether being connected to the first upper support at a location intermediate to the front and rear of the upper support body portion.

* * * * *